US007335638B2

(12) United States Patent
Higuchi

(10) Patent No.: US 7,335,638 B2
(45) Date of Patent: Feb. 26, 2008

(54) PREVENTION AND TREATMENT OF MYCOPLASMA-ASSOCIATED DISEASES

(76) Inventor: Maria De Lourdes Higuchi, Rua Capote Valente, 361-Ap., Sao Paulo (BR) 05409-001

( * ) Notice: Subject to any disclaimer, the term of this patent is extended or adjusted under 35 U.S.C. 154(b) by 90 days.

(21) Appl. No.: 10/952,003

(22) Filed: Sep. 28, 2004

(65) Prior Publication Data

US 2005/0142116 A1 Jun. 30, 2005

Related U.S. Application Data

(63) Continuation-in-part of application No. PCT/BR03/00049, filed on Mar. 28, 2003, and a continuation-in-part of application No. 10/086,913, filed on Mar. 1, 2002, now Pat. No. 7,108,851, which is a continuation of application No. PCT/BR01/00083, filed on Jul. 3, 2001.

(30) Foreign Application Priority Data

| Jul. 3, 2000 | (BR) | .................................. 0002989 |
| Jul. 3, 2001 | (BR) | .................................. 0102648 |
| Mar. 28, 2002 | (BR) | .................................. 0201010 |

(51) Int. Cl.
*A61K 38/00* (2006.01)
*C12Q 1/68* (2006.01)

(52) U.S. Cl. ............................................ 514/12; 435/6
(58) Field of Classification Search .................. 514/12; 435/6
See application file for complete search history.

(56) References Cited

U.S. PATENT DOCUMENTS 5,596,091 A * 1/1997 Switzer ...................... 536/24.5
6,281,199 B1 8/2001 Gupta

OTHER PUBLICATIONS

Amaya, et al., 2004, "Structural Insights into the catalytic mechanism of *Trypanosoma cruzi* trans-sialidase" Structure, vol. 12, pp. 775-784.
Kaji, et al., 2005, "A Side effect of neuraminidase inhibitor in a patient with liver cirrhosis" J. Infect. Chemother, 11:41-43.
Higuchi, 2004, "*Trypanosoma cruzi* trans-sialidase as a new therapeutic tool in the treatment of chronic inflammatory diseases: possible action against mycoplasma and chlamydia" Medical Hypotheses, 63, 616-623.
Higuchi, et al., 2003, "Coinfection with *Mycoplasma pneumoniae* and *Chlamydia pneumoniae* in ruptured plaques associated with acute myocardia infarction" Arq. Bras Cardiol, vol. 81, No. 1, 12-22.
Watts, et al., 2003,"*Trypanosoma cruzi* trans-sialidase operates through a covalent sialyl-enzyme intermediate: Tryosine is the catalytic nucleophile" by J. Am. Chem. Soc. 125, 7532-7533.

Aiello, et al., 2002, "A possible role for complement in the pathogenesis of chronic chagasic cardiomyopathy" Journal of Pathology, 197; 224-229.
Buschiazzo, et al., 2002, "The Crystal Structure and Mode of Action of Trans-sialidase, a key enzyme in *Trypanosoma cruzi* pathogenesis," Molecular Cell, vol. 10, 757-758.
Umezawa et al., 2001, "Enzyme-linked immunosorbent assay with *Trypanosoma cruzi* excreted-secreted antigens (TESA-ELISA) for serodiagnosis of acute and chronic Chagas' disease," Diagn. Microbiol. Infect. Dis. 39:169-176 (USA).
Dallo, et al., 2000, Intracellular DNA replication and long term survival of pathogenic mycoplasmas Microbial Pathogenesis, 29: 301-309.
Higuchi et al., 2000, "Great amount of *C. pneumoniae* in ruptured plaque vessel segments at autopsy. A comparative study of stable plaques," Ara. Bras. Cardiol. 74:149-151.
Horne et al., 2000, "IgA sero-positivity to *Mycoplasma pneumoniae* predicts the diagnosis of coronary artery disease," J. Am. Coll. Cardiol. 35:321 (abstract).
Laroy et al., 2000, "Cloning of *Trypanosoma cruzi* trans-Sialidase and Expression in *Pichia pastoris*," Protein Expr. Purif. 20:389-393.
Maraha et al., 2000, "Is *Mycoplasma pneumoniae* associated with vascular disease," J. Clin. Microbiol. 38:935-936.
Palomino, et al., 2000, Systematic mapping of hearts from chronic chagasic patients: the association between the occurrence of histopathological lesions and *Trypanosoma cruzi* antigens Annals of Tropical Medicine and Parasitology, vol. 94, No. 6, 571-579.
Sambiase et al., 2000, "CMV and transplant-related coronary atherosclerosis: an immunohistochemical, in situ hybridization and polymerase chain reaction in situ study," Modern Pathology 13:173-179.
Treanor, et al., 2000, "Efficacy and Safety of the Oral Neuraminidase Inhibitor Oseltamivir in Treating Acute Influenza" JAMA, vol. 283.
Berbec et al., 1999, "Total serum sialic acid concentration as a supporting marker of malignancy in ovarian neoplasia," Eur J Gynaecol On col 20(5-6): 389-392.
Buscaglia et al., 1999, "Tandem amino acid repeats from *Trypanosoma cruzi* shed antigens increase the half-life of proteins in blood", Blood, 93:2025-2032.
Cole, 1999, "Mycoplasma-induced arthritis in animals: relevance to understanding the etiologies of the human rheumatic diseases," Rev. Rhum. Engl. Ed. 66 (1 Suppl):45S-49S.
Feng Shaw-Huey, et al., 1999, "Mycoplasma infections prevent apoptosis and induce malignant transformation of interleukin-3-dependent 32D hematopoietic cells," Mol Cel Biol 19(12): 7995-8002.
Monto, et al., 1999, "Efficacy and Safety of the Neuraminidase Inhibitor Zanamivir in the treatment of Influenza A and B Virus Infections" Journal of Infectious Diseases, 180; 254-61.
Nicolson et al., 1999, "Mycoplasmal infections in chronic illnesses," (http://www.gulfwarvets.com/article24.htm), also published in Medical Sentinel, 4: 172-175,191.

(Continued)

Primary Examiner—Maryam Monshipouri
(74) Attorney, Agent, or Firm—Baker Botts LLP

(57) ABSTRACT

The invention relates to the prevention and treatment of diseases associated with undesirable cell proliferation comprising preventing and treating mycoplasma and other microorganism co-infection. It is based, at least in part, on the discovery that, in many cases, mycoplasma infection exists coincident with a second microorganism.

5 Claims, 15 Drawing Sheets

OTHER PUBLICATIONS

Ros-Bullon, et al., 1999, "Serum sialic acid in malignant melanoma patients: na ROC curve analysis," Anticancer Res 19(4C): 3619-3622.

Buscaglia et al., 1998, "The repetitive domain of *Trypanosome cruzi* trans-sialidase enhances the immune response against the catalytic domain," J. Infect. Dis. 177(2):431-436.

Fu et al., 1998, "Middle cerebral artery occlusion after recent *Mycoplasma pneumoniae* infection," J. Neurol. Sci. 157:113-115.

Neyrolles et al., 1998, "Identification of two glycosylated components of *Mycoplasma penetrans*: a surface-exposed capsular polysaccharide and a glycolipid fraction," Microbiology, 144:1247-1255.

Razin et al., 1998, "Molecular biology and pathogenicity of mycoplasmas," Microbiol. Mol. Biol. Rev. 62(4):1094-1156.

Taylor-Robinson and Thomas, "*Chlamydia pneumoniae* in arteries: the facts, their interpretation, and future studies," J. Clin. Pathol. 51:793-797 (1998).

Agusti et al., "The trans-sialidase of *Trypanosome cruzi* is anchored by two different lipids," Glycobiology 7(6):731-735 (1997).

Cole, "Mycoplasma interactions with the immune system: implications for disease pathology," 1997, http://www.compkarori.com/arthritis/pil6002.htm).

Danesch et al., Chronic infecFarraj et al., "Mycoplasma-associated pericarditis, case report," Mayo Clin. Proc. 72:33-36 (1997).

Farraj et al., "Mycoplasma-associated pericarditis, case report," Mayo Clin. Proc. 72:33-36 (1997).

Gurfinkel et al., "IgG antibodies to chlamydial and mycoplasma infection plus C-reactive protein related to poor outcome in unstable angina," Arch. Inst. Cardiol. Mex. 67:462-468 (1997).

Higuchi, et al., "Association of an increase in CD8+ T cells with the presence of *Trypanosoma cruzi* antigens in chronic human chagasic mycoarditis," Am. J.Trop. Med. Hyg., 56(5), 1997, pp. 485-489.

Perez et al., "Leukocytoclastic vasculitis and polyarthritis associated with *Mycoplasma pneumoniae* infection," Clin. Infect. Dis. 25:154-155 (1997).

Ribeirão et al., "Temperature differences for trans-glycosylation and hydrolysis reaction reveal an acceptor binding site in the catalytic mechanism of *Trypanosoma cruzi* trans-sialidase," Glycobiology 7:1237-1246 (1997).tion and coronary artery disease: is there a link?, Lancet 350:430-436 (1997).

Buschiazzo et al., "Medium scale production and purification to homogeneity of a recombinant trans-sialidiase from *Trypanosoma cruzi*," Cell Mol. Biol. 42:703-710 (1996).

Cremona et al., "Effect of primary structure modifications in *Trypanosoma cruzi* neuramindase trans-sialidase activities," Cell. Mol. Biol. 42:697-702 (1996).

Sachse et al., 1996, "Mechanisms and factors involved in *Mycoplasma bovis* adhesion to cells," Int. J. of Med. Microbiology 284:80-92.

Smith et al., *Trypanosoma cruzi* trans-silaidase, Accession No. BAA09333, GI:84706, 964 aa, (1996).

Smith et al., *Trypanosoma cruzi* trans-silaidase, Accession No. BAA09334, GI:840708, 1060 aa, (1996).

Umezawa et al., "Immunoblot assay using excreted/secreted antigens of *Trypanosoma cruzi* in serodiagnosis of congenital, acute and chronic Chagas' disease,"J. Clin. Microbiol. 34: 2143-2147, (1996).

Cremona et al., "A single tyrosine differentiates active and inactive *Trypanosome cruzi* trans-sialidase," Gene 160:123-128 (1995).

Tsai et al., 1995, Mycoplasmas and oncogenesis: persistent infection and multistage malignant transformation, Proc Natl Acad Sci U S A.;92(22):10197-201.

Uemura et al., *Trypanosoma cruzi* TCTS-121 gene for trans-sialidase, Accession No. D50685, GI:840707, 3183 bp, (1995).

Uemura et al., *Trypanosoma cruzi* TCTS-154 gene for trans-sialidase, Accession No. D50684, GI:840705, 2895 bp, (1995).

Briones et al.., *Trypanosoma cruzi* trans-sialidase homologue, Accession No. AAC98544, GI:624626, 736 aa, (1993).

Blanchard et al., "AIDS-associated mycoplasmas," Annu. Rev. Microbiol. 48:687-712 (1994).

Campetella et al., "A recombinant *Trypanosoma cruzi* trans-sialidase lacking the amino acid repeats retains the enzymatic activity," Mol. Biochem. Parasitol. 64:337-340 (1994).

Schenkman et al., "A proteolytic fragment of *Trypanosoma cruzi* trans-sialidase lacking the carboxy-terminal domain is active, monomeric, and generates antibodies that inhibit enzymatic activity" J. Biol. Chem. 269:7970-7975 (1994).

Schenkman et al., "Structural and functional properties of Trypanosome trans-sialidase," Annu. Rev. Microbiol. 48:499-523 (1994).

Scudder et al., "Enzymatic characterization of beta-D-galactoside alpha 2,3-trans-sialidase from *Trypanosome cruzi*," J. Biol. Chem. 268(13):9886-9891 (1993).

Parodi et al., "Identification of the gene(s) coding for the trans-sialidase of *Trypanosome cruzi*" EMBO J. 11:1705-1710 (1992).

Schenkman et al., "*Trypanosoma cruzi* trans-sialidase and neuraminidase activities can be mediated by the same enzymes," J Exp Med 175(2):567-575 (1992).

Simecka et al., "Mycoplasmas Diseases of Animals," in Maniloff et al. Eds., Mycoplasmas. Molecular Biology and Pathogenesis, American Society for Microbiology, pp. 391-415 (Washington, 1992).

Uemura et al., "Only some members of a gene family in *Trypanosome cruzi* encode proteins that express both trans-sialidase and neuraminidase activities," EMBO J. 11:3837-3844 (1992).

Vandekerckhove et al., "Substrate specificity of the *Trypanosoma cruzi* trans-sialidase," Glycobiology 2(6):541-548, (1992).

Pollevick et al., "The complete sequence of a shed acute-phase antigen of *Trpanosoma cruzi*," Mol. Biochem. Parasitol. 47:247-250 (1991).

Schenkman et al., "Attachment of *Trypanosoma cruzi* trypomastigotes to receptors at restricted cell surface domains," Exp. Parasitol. 72:76-86 (1991).

Roberts et al., "Sialic Acid-dependent Adhesion of *Mycoplasma pneumoniae* to Purified Glycoproteins," Journal of Biological Chemistry, 264:9289-9293 (1989).

Highuci, et al., "The role of active myocarditis in the development of heart failure in chronic chagas disease : a study based on endomycardial biopsies," Clin. Cardiol. 10, 665-670 (1987).

Chen et al., "Carditis associated with *Mycoplasma pneumoniae* infection," Am. J. Dis. Child. 140:471-472 (1986).

Izumikawa et al., 1986, "*Mycoplasma pneumoniae* attachment to glutaraldehyde-treated human WiDr cell cultures" Proc. Soc. Exp. Biol. Med.

Libby, et al., "A Neuraminidase from *Trypanosoma cruzi* removes sialic acid from the surface of mammalian myocardial and endothelial cells," J. Clin. Invest., vol. 77, Jan. 1986, 127-135.

Kahane, "Purification of attachment moiety: a review," Yale J. Biol. Med. 53:665-669 (1983).

Maida, 1983, "Immunological reactions against *Mycoplasma pneumoniae* in multiple sclerosis: preliminary findings," J. Neurol. 229(2):103-111.

Pereira, "A developmentally regulated neuraminidase activity in *Trypanosoma cruzi*," Science 219:1444-1446 (1983).

Baseman et al., "Sialic acid residues mediate *Mycoplasma pneumoniae* attachment to human and sheep erythrocytes," Infect. Immun. 38(1):389-391 (1982).

Bredt et al., "Adherence of mycoplasmas: phenomena and possible role in the pathogenesis of disease," Infection 10(3):199-201 (1982).

Chandler et al., "*Mycoplasma pneumoniae* attachment: competitive inhibition by mycoplasmal binding component and by sialic acid-containing glycoconjugates," Infect. Immun. 38(2):598-603 (1982).

Krause et al., "Identification of *Mycoplasma pneumoniae* proteins associated with hemadsorption and virulence," Infect. Immun. 35:809-817 (1982).

Hansen et al., "Characterization of hemadsorption-negative mutants of *Mycoplasma pneumoniae*," Infect. Immun. 32:127-136 (1981).

Kahane et al., "Attachment of mycoplasmas to erythrocytes: a model to study mycoplasma attachment to the epithelium of the host respiratory tract," Isr. J. Med. Sci. 17:589-592 (1981).

Taylor-Robinson et al., "Mycoplasmal adherence with particular reference to the pathogenicity of *Mycoplasma pulmonis*," Isr. J. Med. Sci. 17:599-603 (1981).

Glasgow and Hill, "Interactions of *Mycoplasma gallisepticum* with sialyl glycoproteins," Infect. Immun. 30:353-361 (1980).

Gabridge and Taylor-Robinson, "Interaction of *Mycoplasma pneumoniae* with human lung fibroblasts: role of receptor sites," Infect. Immun. 25:455-459 (1979).

Clyde et al., "Tropism for *Mycoplasma gallisepticum* for arterial walls," Proc. Natl. Acad. Sci. U.S.A. 70: 1545-1549 (1973).

Collier and Clyde, "Relationships between *M. pneumoniae* and human respiratory epithelium," Infect. Immun. 3:694-701 (1971).

Sobeslavsky, et al., 1968, Adsorption of *Mycoplasma pneumonia* to neuraminic acid receptors of various cells and possible role in virulence by Journal of Bacteriology, p. 695-705.

Higuchi et al., 2006, "Co-infection ratios versus inflammation, growth factors and progression of early atheromas," APMIS, 114(5):338-44.

Damy et al,. "Coinfection of laboratory rats with *Mycoplasma pulmonis* and *Chlamydia pneumoniae*," Contemp. Top.Am.Assoc. Lab.An.Sci. 42: 52-56 (2003).

Higuchi, et al., 2003, "Pathophysiology of the heart in chagas' disease: current status and new developments" European Society of Cardiology, pp. 96-107.

Chen et al., "Apoptosis of hepatoma cells SMMC-7721 induced by *Ginkgo biloba* seed polysaccharide," World J. Gastroenterol. 8: 832-6 (2002).

Fearon et al., "Cancer cachexia," Int. J. Cardiol 85: 73-81 (2002).

Giles et al., "Androgenetic alopecia and prostate cancer: findings from an Australian case-control study," Cancer Epidemiol. Biomarkers Prev 11: 549-553 (2002).

Higuchi et al., "*Mycoplasma pneumoniae* and *Chlamydia pneumoniae* in calcified nodules of aortic stenotic valves," Rev Inst Med trop S.Paulo 44:209-212 (2002).

Huber J et al., "A new phylum of Archaea represented by a nanosized hyperthermophilic symbiont," Nature 417: 63-67 (2002).

Mühlradt, "Immunomodulation by mycoplasmas: artifacts, facts and active molecules," in Molecular Biology and Pathogenicity of Mycoplasmas. Eds Razin S & Herrman R, 2002, academic Kluwer/Plenum Publishers, New York, p. 445-472.

Razin et al. Eds., Molecular biology and pathogenicity of mycoplasmas, Kluwer Academic/Plenum Publishers (New York, 2002) (Table of Contents Only).

Sengupta A et al., "Administration of garlic and tomato can protect from carcinogen induced clastogenicity," Nutrit. Res. 22: 859-866 (2002).

Timms, "Vertex baldness link to prostate cancer," Lancet Oncology 3:584 (2002).

Uchide et al., "Effect of antioxidants on apoptosis induced by influenza virus infection: inhibition of viral gene replication and transcription with pyrrolidine dithiocarbamate," Antiviral Res. 56: 207-217 (2002).

Walsmith et al., "Cachexia in rheumatoid arthritis," Int. J. Cardiol. 85: 89-99 (2002).

Wang et al., "The role of endotoxin, TNF-alpha, and IL-6 in inducing the state of growth hormone insensitivity," World J. Gastroenterol. 8: 531-536 (2002).

Akira et al., "Toll-like receptors: critical proteins linking innate and acquired immunity," Nature Immunol. 2:675-680(2001).

Amend et al., "Energetics of overall metabolic reactions of thermophilic and hyperthermophilic archaea and bacteria," F.E.M. S. Microbiol. Rev. 25: 175-243 (2001).

Milner, "A historical perspective on garlic and cancer," J. Nutr. 131: 1027S-1031S. (2001).

Florin THJ et al., "Shared and unique environmental factors determine the ecology of methanogens in humans and rats," Am. J. Gastroenterol. 95: 2872-2879 (2000).

Higuchi et al., 2000, "Detection of *Mycoplasma pneumoniae* and *Chlamydia pneumoniae* in ruptured atherosclerotic plaques," Braz. J. Med. Biol. Res. 33:1023-1026.

Howland et al., The surprising archaea. Discovering another domain of life. Oxford University Press. (New York, 2000). (Table of Contents Only).

Rodrigues-Amaya, "Latin American food sources of carotenoids," Arch. Latinoam. Nutr. 49: 74S-84S (1999).

Woody et al., "Prolactin exerts hematopoietic growth-promoting effects in vivo and partially counteracts myelosuppression by azidothymidine," Exp. Hematol. 27: 811-816 (1999).

Richards et al., "Prolactin is an antagonist of TGF-beta activity and promotes proliferation of murine B cell hybridomas," Cel. Immunol. 184: 85-91 (1998).

Winther et al., "Effects of *Ginkgo biloba* extract on cognitive function and blood pressure in elderly subjects," Curr. Therap. Res. 59: 881-888 (1998).

Danesh et al., "Chronic infections and coronary artery disease: is there a link?", Lancet 350:430-436 (1997).

Ong et al., "Detection and widespread distribution of *Chlamydia pneumoniae* in the vascular system and its possible implications," J. Clin. Pathol. 49:102-106 (1996).

Maniloff et al. Eds., Mycoplasmas, Molecular Biology and Pathogenesis. American Society for Microbiology. (Washington, 1992). (Table of Contents).

Uemura et al., *Trypanosoma cruzi* trans-sialidase-neuraminidase, Accession No. S28409, GI:323067, 200 aa, Jan. 2000.

Pereira et al., "The *Trypanosoma cruzi* neuraminidase contains sequences similiar to bacterial neuraminidases, YWTD repeats of the low density lipoprotein receptor, and Type III modules of fibronection," J. Ex. Med. 174:179-191 (1991).

Val'kovich, 1980, "Viral and mycoplasma-induced glomerulopathies in children," Arkh. Pathol. 42(3):10-15. (Article is in the Russian language. English abstract is provided).

Pereira et al., "Lectin receptors as markers for *Trypanosoma cruzi*. Development stages and a study of the interaction of wheat germ agglutinin with sialic acid residues on epimastigotes cells," J. Exp. Med., 152:1375-1392 (1980).

Woese et al., "Phylogenetic structure of the prokaryotic domain: the primary kingdoms," Proc Natl. Acad. Sci. U.S.A. 74: 5088-5090 (1977).

* cited by examiner

PREVENTION AND TREATMENT OF MYCOPLASMA-ASSOCIATED DISEASES

The present invention is a continuation-in-part of International Patent Application No. PCT/BR03/00049, filed Mar. 28, 2003, published on Oct. 9, 2003 in English as Internation Patent Publication No. WO03/082324, which claims priority to Brazilian Patent Application No. PI 0201010-0, filed Mar. 28, 2002, which is incorporated herein in its entirety. The present invention is also a continuation-in-part of U.S. patent application Ser. No. 10/086,913, filed Mar. 1, 2002, now U.S. Pat. No. 7,108,851 issued Sep. 19, 2006, which is a continuation of International Patent Application No. PCT/BR01/00083, filed Jul. 3, 2001, which claims priority to Brazilian Patent Application Nos. PI 0002989-0, filed Jul. 3, 2000, and PI 0102648-8, filed Jul. 3, 2001, each of which is incorporated herein in their entireties.

The present invention is related to the prevention and treatment of diseases exhibiting undesirable cell proliferation, which may be accompanied by fibrosis, including cutaneous thickening and organ sclerosis. The present invention relates to compositions and methods directed against the microorganisms associated with the disorder, such as mycoplasma and/or a second or third microorganism. It is based, at least in part, on the discovery that, in disease lesions, the mycoplasma infection is closely associated with the presence of at least one other microorganism. In particular, the additional microorganism(s) may be an archaea, a *chlamydia*, and/or a spirochete.

BACKGROUND OF THE INVENTION

Mycoplasmas are the smallest self-replicating microorganisms and have unique properties among the prokaryotes, such as (i) their need for cholesterol to maintain their membrane envelope and (ii) the absence of an external wall. Mycoplasmas are known to cause pulmonary infection in humans. See, Razin et al., "Molecular biology and pathogenicity of mycoplasmas," Microbiol, and Molecular Biology Review; 62(4): 1094-1156, (1998). Furthermore, it is widely known that mycoplasmas can cause disease in most animals, including animals of commercial importance to the husbandry industry, such as cattle, swine, and fowl. See, Maniloff et al. Eds., *Mycoplasmas, Molecular Biology and Pathogenesis*, American Society for Microbiology (Washington, 1992).

It has been suggested that mycoplasma may play a role in the pathogenesis of a number of other diseases, including asthma, diseases of the large intestine, rheumatoid diseases such as rheumatoid arthritis, maculopapular erythemas, stomatitis, conjunctivitis, pericarditis, Alzheimer's Disease, multiple sclerosis, the sequelae of AIDS and HIV infection, genito-urinary infections, Chronic Fatigue Syndrome, and Gulf War Syndrome. However, the actual role of mycoplasmas in these various diseases have been difficult to determine, because most of the associations drawn to mycoplasma nfection are based on serologic evidence rather than direct observation of mycoplasmaorganisms in disease lesions. See, Cole, "Mycoplasma interactions with the immune system: implications for disease pathology," (http://www.compkarori.com/arthritis/pi16002.htm);Cole, "Mycoplasma-induced arthritis in animals: relevance to understanding the etiologies of the human rheumatic diseases," *Rev. Rhum. Engl. Ed.;* 66(1 Suppl):45S-49S (1999); and Nicolson et al., "Mycoplasmal Infections in Chronic Illnesses," (http://www.gulfwarvets.com/article24.htm).

Mycoplasma and chlamydia have both been implicated in vascular disease, but the etiologic relationships have not been confirmed. See, Chen et al., "Carditis associated with Mycoplasma pneumoniae infection," *Am. J. Dis. Child.* 140:471-472 (1986); Clyde et al., "Tropism for Mycoplasma gallisepticum for arterial walls," *Proc. Natl. Acad. Sci. U.S.A.* 70::1545-1549 (1973); Danesch et al., "Chronic infections and coronary artery disease: is there a link?", *Lancet* 350:430-436 (1997); Farraj et al., "Mycoplasma-associated pericarditis, case report," *Mayo Clin. Proc.* 72:33-36 (1997); Fu et al., "Middle cerebral artery occlusion after recent Mycoplasma pneumoniae infection," *J. Neurol. Sci.* 157:113-115 (1998); Gurfinkel et al., "IgG antibodies to *chlamydial* and mycoplasmainfection plus C-reactive protein related to poor outcome in unstable angina," *Arch. Inst. Cardiol. Mex.* 67:462-468 (1997); Ong et al., "Detection and widespread distribution of *Chlamydia pneumoniae* in the vascular system and its possible implications," *J. Clin. Pathol.* 49:102-106 (1996); Perez et al., "Leukocytoclastic vasculitis and polyarthritis associated with Mycoplasma pneumoniae infection," *Clin. Infect. Dis.* 25:154-155 (1997); Taylor-Robinson and Thomas, "*Chlamydia pneumoniae* in arteries: the facts, their interpretation, and future studies," *J. Clin. Pathol.* 51:793-797 (1998). In Maraha et al., "Is Mycoplasma pneumoniae associated with vascular disease," *J. Clin. Microbiol.* 38:935-936 (February 2000), it was stated that "in a serological study, in contrast to *C. pneumoniae* antibodies, *M. pneumoniae* antibodies are not associated with recurrent events in patients with unstable angina", citing Gurkinkel et al., supra. Maraha et al. reported that using PCR, they "were unable to detect *M. pneumoniae* in the great majority of the 103 tested specimens" of atherectomies and degenerative heart valves, and concluded that "the results . . . do not support the hypothesis that *M. pneumoniae* is an important factor in the development of vascular disease. In contrast, Home et al. have published a correlation between a positive serology for Mycoplasma pneumoniae and atherosclerosis (Home et al., "IgA seropositivity to Mycoplasma pneumoniae predicts the diagnosis of coronary artery disease," *J. American Coll. Cardiol.* 35:321 (abstract) (2000)).

Frequent co-occurrence of mycoplasmawith other microorganisms, such as *chlamydia*, have been observed in cell proliferation diseases (International Patent Application No. PCT/BR01/00083, filed Jul. 3, 2001 and BR PI 0002989-0, filed Jul. 3, 2001). This association appears to contribute to increasing the virulence of both pathogens. For example, HIV patients, who have positive serology for Mycoplasma penetrans, are in worse clinical health than HIV patients who test negative for Mycoplasma penetrans. See, Blanchard et al., "AIDS-associated *mycoplasmas* ," *Annu. Rev. Microbiol.*, 48:687-712, (1994). Mycoplasmal lipoproteins are potent macrophage activators and have comparable activity and equally wide-spread in mollicutes as is LPS in Gram-negative bacteria. See, Razin et al. Eds., *Molecular biology and pathogenicity of mycoplasmas, Kluwer Academic/Plenum Publishers (New York,* 2002). Recently described different toll-like receptors (TLR) in macrophages that are activated by products from pathogens such as mycoplasmal lipoproteins and LPS from bacteria have demonstrated to be important for activation of the immune system and that the efficacy of immune response depends on which concomitant TLR s are activated. See, Akira et al., "Toll-like receptors: critical proteins linking innate and acquired immunity," Nature Immunol. 2:675-680(2001).

Archaea are the most ancient microorganisms existing in nature, but have been characterized only recently. See, Woese et al., "Phylogenetic structure of the prokaryotic domain: the primary kingdoms," *Proc Natl. Acad. Sci. U.S.A.* 74: 5088-5090 (1977). They inhabit extreme environments and are constituted by lipid monolayer membranes. Rich alkaline atmosphere with sodium ions and metals prevents proliferation of other bacteria, but is favorable to archaea's growth. Archaea have been isolated from alkaline waters from the Dead Sea, the Great Salt Lake and Yellowstone National Park. They have a small size, can—just barely—be viewed with an optical microscope, and observation of structural details requires electron microscopy. See, Howland et al., *The surprising archaea. Discovering another domain of life*, Oxford University Press (New York, 2000). Some are considered hyperthermophilic as they survive in very high temperatures.

Another unusual characteristic of some archaea is that they appear to use metal as an energy source. See, Amend et al., "Energetics of overall metabolic reactions of thermophilic and hyperthermophilic Archaea and bacteria," *F.E.M.S. Microbiol. Rev.* 25: 175-243 (2001). It is considered that archaea usually need an anaerobic or nearly anaerobic environments to carry out oxidation-reduction reactions with participation of different chemical compounds, including metals. See, Amend et al., "Energetics of overall metabolic reactions of thermophilic and hyperthermophilic Archaea and bacteria," *F.E.M.S. Microbiol. Rev.* 25: 175-243 (2001).

Recently, a new kind of extremely small archaea, which is dependent on bigger archaea, was described and named nanoarchaea. See, Huber J et al., "A new phylum of Archaea represented by a nanosized hyperthermophilic symbiont," *Nature* 417: 63-67 (2002). With the exception of archaea that reside in the mammalian intestine and produce methane gases, there is no report of archaea existing within plants or animals. See, Florin T H J et al., "Shared and unique environmental factors determine the ecology of methanogens in humans and rats," *Am. J. Gastroenterol.* 95: 2872-2879 (2000).

SUMMARY OF THE INVENTION

The present invention relates to compositions and methods for the prevention and treatment of disorders associated with mycoplasma and one or more non-mycoplasma microorganism. It is based, at least in part, on the discovery that mycoplasma infection associated with cell proliferation was accompanied by the presence of a non-mycoplasma microorganism and exhibited increased fibrosis, including organ sclerosis and cutaneous thickening. This second microorganism is a *chlamydia* and/or an archaea and/or a spirochete. In a preferred embodiment of the invention, the second microorganism is archaea.

The present invention provides for compositions comprising an effective amount of one agent or more which prevents or inhibits the proliferation of mycoplasma and/or its associated non-mycoplasma microorganism.

The agent may be one or more antibiotic directed at treating mycoplasma and/or the non-mycoplasma microorganism.

Alternatively, the agent is a particle containing DNA or RNA, such as an archaea or a nanoarchaea. When the agent is a nanoarchaea, the particle may also be called a nanoparticle. The source of this particle may be a plant or a thermal water. The liquid for proliferation of these particles may be a liquid presenting some of these characteristics: extremely high or low pH, extremely high temperature and solvents.

Alternatively, the agent is a protein capable of removing sialic acid residues, such as a neuraminidase enzyme or preferably a trans-sialidase enzyme, wherein removal of the sialic acid inhibits or prevents the attachment of mycoplasma and/or non-mycoplasma microorganism to the host cells. In preferred embodiments of the invention, the agent is the trans-sialidase enzyme of *Trypanosoma cruzi*, or a portion or variant of the native enzyme which has trans-sialidase activity.

In addition, the present invention provides for compositions that further comprise a combination of one or more of the agents selected from the group consisting of a homeopathic drug, an antibiotic, a chelant of metal, and a cytokine.

The present invention also provides for methods of preventing and/or treating disorders manifested by cell proliferation associated with increased fibrosis and/or co-existent proliferation of mycoplasm and one or more additional microorganism, whereby a subject is administered a composition of the present invention comprising an effective amount of one agent or a combination of agents which prevents or inhibits the proliferation and/or pathogenicity of mycoplasma and its associated non-mycoplasma microorganism.

The disorders to be treated according to the present invention include, but are not limited to, aortic valve stenosis, Lyme's disease, psoriasis, lymphocytic chronic arteritis, non purulent inflammatory osteoarthritis, glomerulonephritis, hepatitis, multiple sclerosis, neoplasias, atherosclerosis, baldness, etc. Without being bound to any particularly theory, it is hypothesized that infection with mycoplasma may inhibit programmed cell death (apoptosis) and favor the proliferation of other infectious microorganisms and development of fibrosis.

The present invention also relates to methods of making the presently disclosed compositions, wherein the agent in the composition is derived from a plant or thermal water. The method comprises obtaining a plant tissue or thermal water sample, culturing the plant tissue or thermal water sample under conditions which promote particle proliferation to produce a culture, filtering the culture using a less than 1.1 μm filter, and concentrating the culture to produce the composition of the present invention.

DETAILED DESCRIPTION OF THE INVENTION

Figure 1:
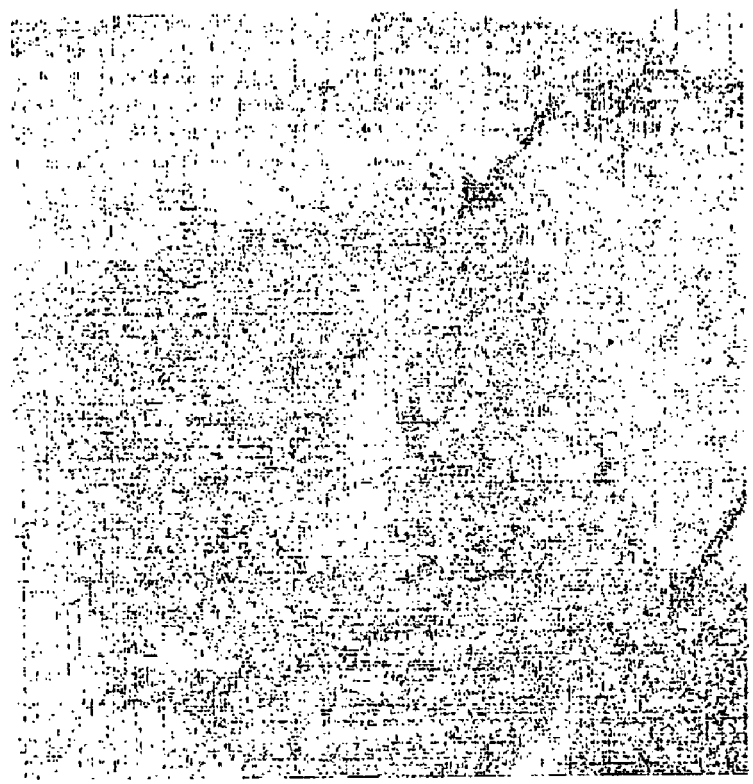
FIG. 1 is a histological section of the human stenotic aortic valve with calcification, presenting positivity for *Chlamydia pneumoniae* antigens (arrows) in calcification foci and in the surrounding fibrosis. (Imunohistochemistry—original magnification: 20×).

The Brazilian patent application, PI 0002989-0, and International Patent Application No. PCT/BR01/00083, relate to the prevention and treatment of diseases associated with undesirable cell proliferation including narrowing of blood vessels and malignancy, comprising preventing or treating a underlying mycoplasma infection. It is based, at least in part, on the discovery that, these disorders cause undesirable cell proliferation and are associated with the presence of mycoplasma and/or proliferation of other infectious organisms.

The present invention relates to compositions and methods for preventing and/or treating conditions characterized by undesirable cell proliferation, which may be associated with fibrosis, and a co-infection by mycoplasma and at least one non-mycoplasma pathogen. The second microorganism may be a virus or a bacteria, such as, for example, *chlamydia*, spirochete, *Helicobacter pylori*, etc. or an archaea. It was observed that in fibrotic tissues of pathological processes, e.g. articular lesions, skin lesions (such as psoriasis and cutaneous ulcers in Lyme-like disease) in laboratory rodents and in humans, a high quantity of mycoplasma were present in close association with other primitive microorganisms, mainly *chlamydia* and/or archaea (in some cases nanoarchaea) and/or spirochetes. The mycoplasma-associated microorganism may be, for example but not by way of limitation, pathogenic archaea and nanoarchaea, *chlamydia* or spirochete. As disclosed in the Examples section, the inventor has observed the presence of a secondary microorganism, i.e. archaea, in lesions associated with mycoplasm infections or mycoplasm-associated disorders. The identification of archaea in these lesions indicate that the archaea appear to have a pathogenic role. The present invention provides a method for the treatment of these mycoplasma and pathogenic archaea-associated disorders by preventing or inhibiting the growth of the mycoplasma and/or archaea. The inventor has also surprisingly discovered that the use of non-pathogenic archaea is effective in treating the above-described disorders.

The present invention provides for compositions comprising an effective amount of one or more agent which prevents or inhibits the mycoplasma and/or its associated non-mycoplasma microorganism associated with various disorders exhibiting undesirable cell proliferation.

In a preferred embodiment of the invention, the agent is a particle containing DNA or RNA, wherein the particle is non-pathogenic archaea and/or nanoarchaea. The particle is present in amounts effective to prevent or inhibit the growth of the mycoplasma and/or archaea.

In an embodiment of the invention, the composition comprises small particles of less than 500 nm in diameter. In another embodiment of the invention, the composition comprises medium particles of between 500 nm and 1.1 μm in diameter. The compositions may comprise a combination of both small and medium particles.

Typically, the size of the particle ranges from 70 nm to 1.1 μm in diameter when in a solution containing about 20% of water. The size of the particle may enlarge or decrease depending on the concentration of water and ions, such as Na+ or Ca+. In an ethanol plant extract derived from a culture of plant in 40:60 ratio between plant and alcohol weight, the particles that are useful for treatment have a less than 0.20 μm diameter. The agent may be a homeopathic drug having an enriched population of non-pathogenic archaea.

The composition comprises an enriched population of particles. In an embodiment of the invention, the composition comprises a concentration of at least $1.0 \times 10^6$ particles/ml, preferably $50 \times 10^6$ particles/ml, more preferably $75 \times 10^6$ particles/ml.

In an embodiment of the invention, the composition comprises a mixed population of particles, having at least $10 \times 10^6$ particles/ml of medium particles and at least $75 \times 10^6$ particles/ml of small particles. In a preferred embodiment of the invention, the composition comprises $27.5 \times 10^6$ particles/ml of medium particles and $80.75 \times 10^6$ particles/ml of small particles.

A comparison of a composition of the present invention with a prior art compostion indicates that the present compositions contain a greater concentration of particles. The examination of Sundown Garlic 1500 oil manufactured for distribution by Rexall Sundown, Inc., (Boca Raton Fla. USA) indicated a concentration of larger and medium particles of $1.9 \times 10^6$/ml and small particles $2.3 \times 10^6$/ml. The examination of a composition of the present invention indicated $27.5 \times 10^6$ particles/ml of medium particles and $80.75 \times 10^6$ particles/ml of small particles.

The characterization of a particle containing DNA or RNA may be performed by direct observation of a drop of the composition to which a drop of a vital DNA stain (acridine orange diluted 1:100 in water) has been added. Other vital dyes, such as bisbenzimide H 33342 (Hoechst) (10 ug/ml), 4',6-diamidino-2-phenylindole, dihydrochloride (DAPI) may also be used. To visualize the particles, a drop (50 ul) of a water solution of potassium sulfate or zinc sulfate (1 mg/ml) may be added. The ions are incorporated and cause the particles to become larger. The dyes may be incorporated in the A-T nucleic acid regions. The particles have a natural movement that increases or decreases upon the addition of these ions.

Electron microscopy may also be used to confirm the identification of archaea by looking for the characteristic double wavy and discontinuous monolayer lipid membrane. Archaea exhibit different shapes and sizes, varying from less than 100 nm to more than 3 μm. In order to obtain a pellet of archaea present in the plant extracts or in the serum of the patient for electron microscopy, a modification in the routine procedure was performed in order to precipitate also the smallest protein and lipidic structures that usually are not retained in centrifuged pellets. 0.5 ml of the liquid was fixed in 0.5 ml of 3% glutaraldehyde for two hours and postfixed with additional 0.5 ml of osmium tetroxide for more two hours; the microlipidic particles became heavy enough to be centrifuged. After that, the preparation was centrifuged for 20 minutes. The supernatant was discarded and the pellet processed as usually to be embedded in araldite. Ultrathin sections of 60 nm thickness were obtained and contrasted with a solution of 5% lead nitrate.

Figure 20:
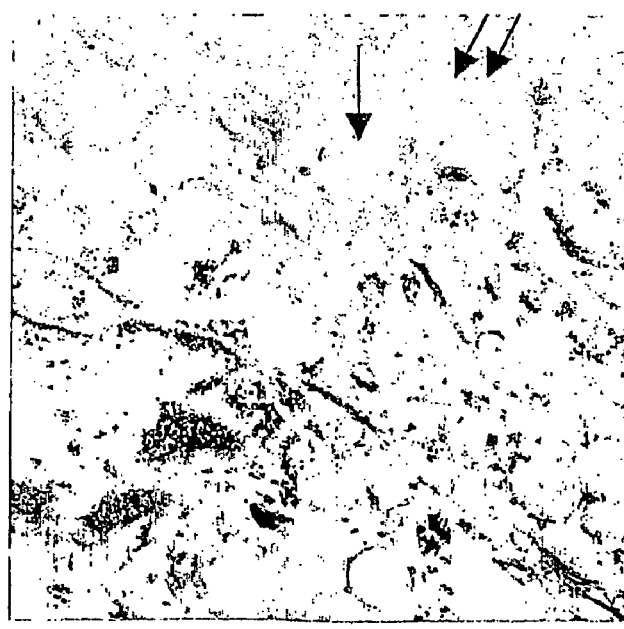
FIG. 20 shows an electron micrograph exhibiting a neoplasic cell from prostate adenocarcinoma containing empty rounded structures compatible with pathogenic archaea (single arrow) and mycoplasma (double arrows) in the cytoplasm, similar to those presenting in FIG. 19.
Figure 18:
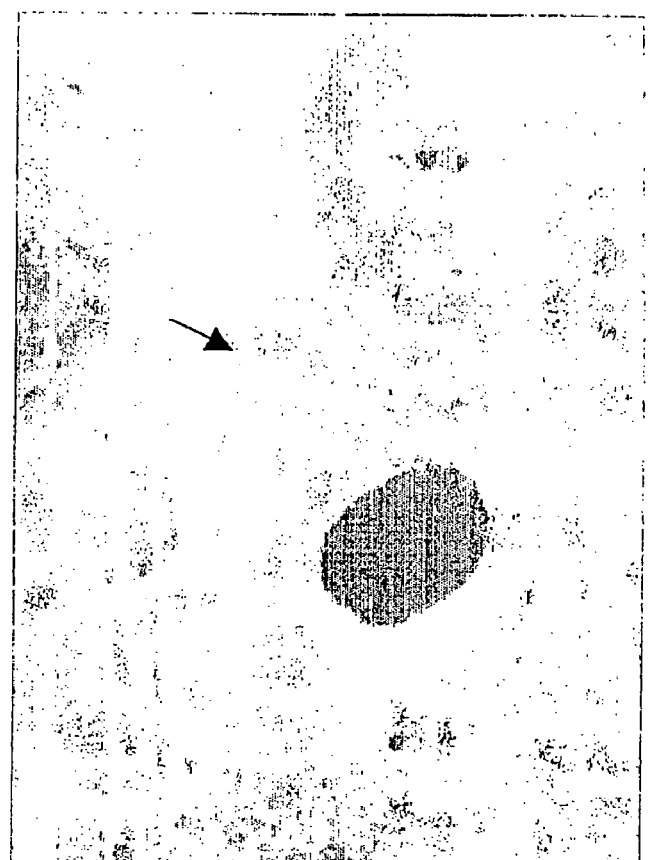
FIG. 18 shows an electron micrograph of a liver from a mouse exhibiting experimental schistosomiasis treatment with trans-sialidase enzyme and *Ginkgo biloba* extract rich in nanosized particles. Four small rounded structures in the lumen of centrolobular vein with morphology from the top to bottom are shown: 1°, archaea extracted from *Ginkgo biloba* that is more electron dense, 2° mycoplasma that presents intermediate electron density and 3°, two pathogenic archaea that are larger and present an empty aspect.
Figure 19:
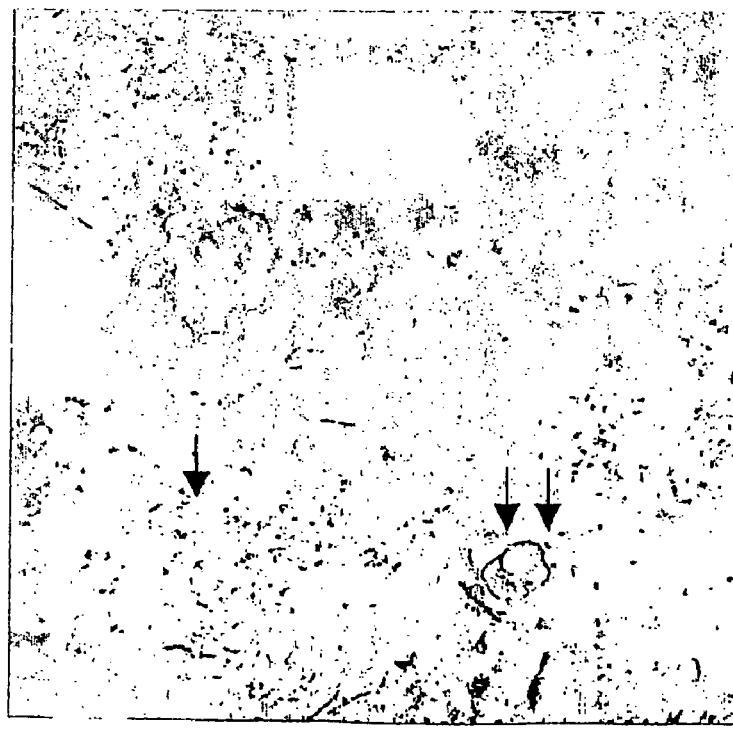
FIG. 19 shows an electron micrograph exhibiting an anexus cell from bald skin presenting large numbers of rounded structures involved by thin membrane without electron dense content compatible with archaea with empty aspect (single arrow) and mycoplasma (double arrow) in the cytoplasm.
Figure 24:
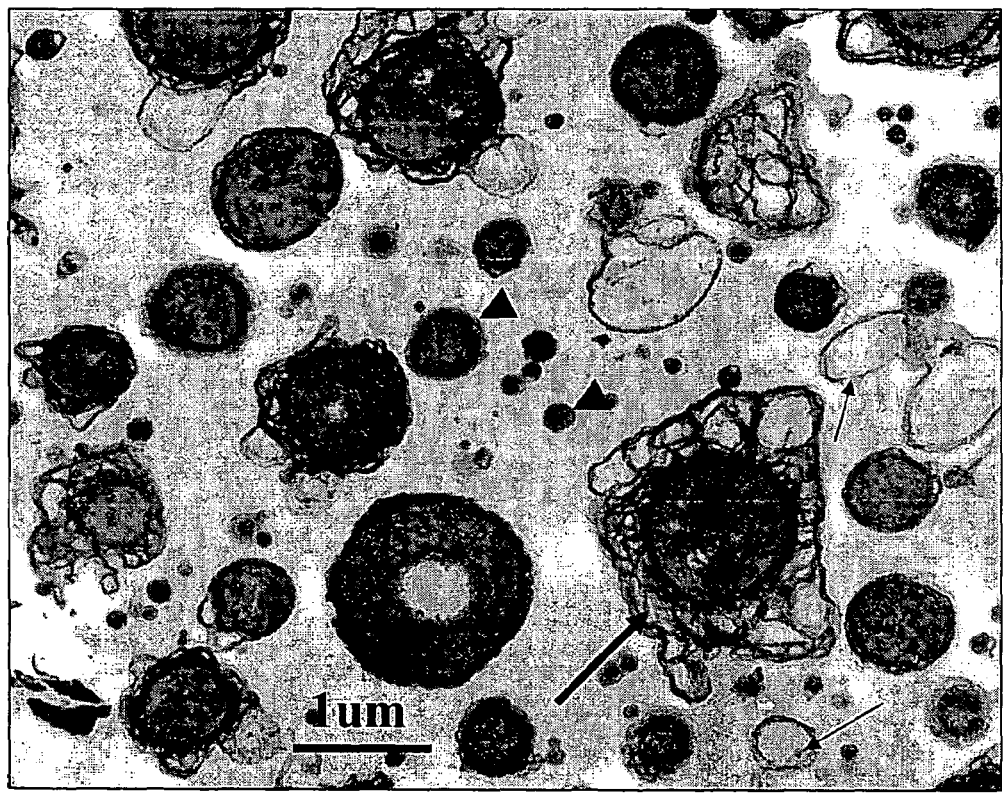
FIG. 24 ahows an electron micrograph of garlic alcoholic extract hydrated with 30% of water presenting archaea and nanoarchaea of different sizes. The pathogenic archaea are probably the archaea with empty aspect and they are attracted by the eletrondense archaea. The larger ones usually are already completely surrounded by the empty archaeas; these archaea possibly are of low efficacy if administered to an individual in order to remove the pathogenic archaea present in the lesions.
Figure 25:
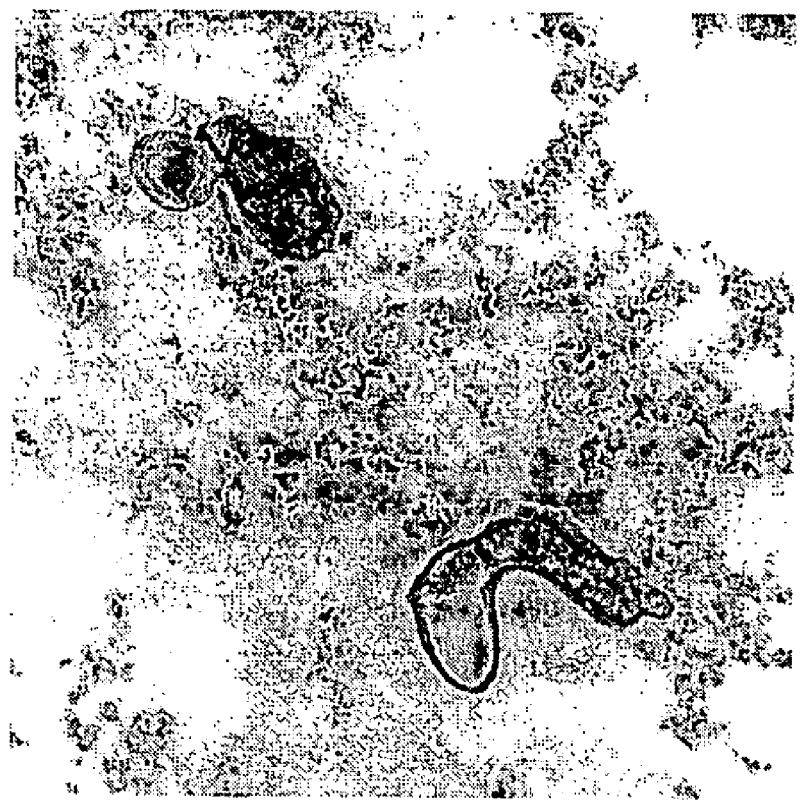
FIG. 25 shows an electron micrograph of the serum of a patient with symptoms of Lyme disease, but negative for *Borrelia burgdorferi*, showing two mycoplasmas that have one envoltory membrane and granulous electron dense material inside. On the top the mycoplasma in intimal contact with a structure with morphology of archaea characterized by thin delicate envoltory lipidic monolayer membrane and having an internal empty space, which is characteristic of the archaea present in tissue lesions.

Electron microscopy revealed two forms of archaea, having different morphological characteristics. One type had electron-dense content and the other type had a clear content. The clear archaea had an empty aspect and had the same morphology of the archaea present in the lesions as demonstrated in FIGS. 19 and 20, present in anexus cells of bald skin and in adenocarcinoma cells from prostate, respectively. The empty archaea and nanoarchaeas were considered pathogenic. Observations at the electron microscopy indicated that the archaea with electron dense content attracted the empty ones. This phenomenon was observed in the electron microscopy analysis of extracts from *Ginkgo biloba* and garlic (FIG. 24) and in mice that had received *Ginkgo biloba* extract that showed aggregates of electron dense *Ginkgo biloba*'s archaea, mycoplasma and empty pathogenic archaea (FIG. 18). The mycoplasma is frequently seen adhered or incorporating empty archaea in the lesions and in the serum of patients (FIG. 25).

Archaea can also be characterized using PCR analysis, employing probes specific to archaea genome. In the present invention, archaea present in garlic and *ginkgo biloba* extracts were also revealed by PCR technique, using the generic primers for archaea as follows:

```
1100Af- 5'-AGTCAGGTAACGAGCGAG-3'    (SEQ ID NO:1)
and
1400Ar 5'-GTGCAAGGAGCAGGGAC-3'.     (SEQ ID NO:2)
```

In an embodiment of the invention, the agent may be a homeopathic drug. Examples of homeopathic drugs include arnica and carbonic calcarea. The homeopathic drug may be useful to prevent growth or decrease the number of mycoplasma and/or non-mycoplasma microorganism in the subject. Alternatively, the homeopathic drug may be useful in favoring or increasing the action of the non-pathogenic particles in the composition. Small amounts of metal or other substances found in the homeopathic drug may interfere with pathogenic archaea metabolism.

In an embodiment of the invention, the agent is an antibiotic. It may be, for example but not way of limitation, erythromycin, azithromycin, clarithomycin, tetracycline, minocycline, clindamycin, ofloxacin, chloramphenicol, methotrexate or any antibiotic known to have activity against mycoplasma-associated microorganism. The dose of antibiotic may be the standard dose or a lower dose.

In an embodiment of the invention, the agent is a protein capable of removing sialic acid residues, such as a neuranimidase enzyme or, more preferably, a trans-sialidase enzyme. In particularly preferred embodiments of the invention, the agent is the trans-sialidase enzyme of *Trypanosoma cruzi*, or a portion or variant of the native enzyme which has trans-sialidase activity.

In an alternative embodiment of the invention, the agent is a chelant of metal like pyrrolidine dithiocarbamate (PDTC). Some compounds that are chelates of metal, such as pyrrolidine dithiocarbamate (PDTC), have an anti-oxidant effect that can be effective in the combat to viral infections and cancers. See, Uchide et al., "Effect of anti-oxidants on apoptosis induced by influenza virus infection: inhibition of viral gene replication and transcription with pyrrolidine dithiocarbamate," *Antiviral Res.* 56: 207-217 (2002).

In an alternative embodiment of the invention, the agent is a cytokine. The cytokine includes, but is not limited to, TNF-alpha, interleukin 6 (IL-6), interleukin 1 (IL-1), growth hormone and prolactin.

The foregoing agents may be comprised in a composition as a single agent or in combination. Preferred combinations include as follows:
  particle derived from plant extract, particle derived from thermal water;
  particle derived from plant extract, trans-sialidase enzyme of *Trypanosoma cruzi*;
  particle derived from thermal water, trans-sialidase enzyme of *Trypanosoma cruzi*;
  particle derived from plant extract, antibiotic;
  particle derived from thermal water, antibiotic;
  trans-sialidase enzyme of *Trypanosoma cruzi*, PDTC;
  particle derived from plant extract, growth hormone;
  particle derived from thermal water, growth hormone;
  particle derived from plant extract, prolactin;
  particle derived from thermal water, prolactin;
  particle derived from plant extract, trans-sialidase enzyme of *Trypanosoma cruzi*; prolactin;
  particle derived from thermal water, trans-sialidase enzyme of *Trypanosoma cruzi*; prolactin;
  particle derived from plant extract, trans-sialidase enzyme of *Trypanosoma cruzi*, growth hormone;
  particle derived from thermal water, trans-sialidase enzyme of *Trypanosoma cruzi*, growth hormone;
  particle derived from plant extract, trans-sialidase enzyme of *Trypanosoma cruzi*, growth hormone, PDTC; and
  particle derived from thermal water, trans-sialidase enzyme of *Trypanosoma cruzi*, growth hormone, PDTC.

It is known from the literature that mycoplasma infection is associated with increased production of many cytokines, e.g. tumoral necrosis factor alpha (TNF-alpha), and oxidation of the host cells. This appears to occur in many chronic inflammatory diseases such as arthritis, pericarditis, Alzheimer's disease, etc. See, Mühlradt, in *Molecular Biology and Pathogenicity of Mycoplasmas*. Eds Razin S & Herrman R, 2002, academic Kluwer/Plenum Publishers, New York. Pg 445-472. Several chronic diseases, such as inter alia cancer, rheumatoid arthritis, cardiac insufficiency, exhibit cachexia and myelodepression associated with an expressive increase in the TNF-alpha in the blood flow and other cytotokines. See, Walsmith et al., "Cachexia in rheumatoid arthritis," *Int. J. Cardiol.* 85: 89-99 (2002) and Fearon et al., "Cancer cachexia," *Int. J. Cardiol* 85: 73-81 (2002). Critical states of diseases, such as sepsis, trauma, burn, cancer and congestive cardiac insufficiency are also associated with increase of some cytokines like TNF-alpha, IL-6 and IL-1. It may also be associated with hypersensitivity to growth hormone, which seems to be related to the presence of bacterial lipopolysaccharide (LPS). See, Wang et al., "The role of endotoxin, TNF-alpha, and IL-6 in inducing the state of growth hormone insensitivity," *World J. Gastroenterol.* 8: 531-536 (2002). Prolactin is a neuroendocrine hormone that improves immunological responses not only in vitro but also in vivo. See, Richards et al., "Prolactin is an antagonist of TGF-beta activity and promotes proliferation of murine B cell hybridomas," *Cel. Immunol.* 184: 85-91 (1998). Prolactin also acts in hematopoietic development and has been suggested to be useful in the treatment of the myelosuppression. See, Woody et al., "Prolactin exerts hematopoietic growth-promoting effects in vivo and partially counteracts myelosuppression by azidothymidine," *Exp. Hematol.* 27: 811-816 (1999).

The composition of the invention may further comprise a suitable pharmaceutical or homeopathic vehicle. The composition may be used together with other agents directed toward treating either the mycoplasma co-infection or the undesirable cell proliferation associated with fibrosis. As a specific example, the above described particles may be used in conjunction with, for the treatment of psoriasis, chemotherapeutic agent or radiation therapy or, for the treatment of an organ sclerosis, a standard anti-inflammatory therapy.

The present invention also relates to methods of making the presently disclosed compositions, wherein the agent in the composition is derived from a plant or thermal water. The method comprises obtaining a plant tissue or thermal water sample, culturing the plant tissue or thermal water sample under conditions which promote particle proliferation to produce a culture, filtering the culture using a less than 1 μm filter, and concentrating the culture to produce the composition.

The particle may be derived from a plant extract. The plant extract may be derived from, for example, garlic, *Ginkgo biloba*, tomato, orchid, guava, Ginseng, *Zingiber* (ginger), and others. The use of plant extracts from tomato, guava (*Psidium guajava*), garlic, *Ginkgo biloba*, etc, for the treatment of many of the above described diseases due to their oxide-reduction and apoptotic properties have been disclosed. See Rodrigues-Amaya, "Latin American food sources of carotenoids," *Arch. Latinoam. Nutr.* 49: 74S-84S (1999); Sengupta A et al., "Administration of garlic and tomato can protect from carcinogen induced clastogenicity," *Nutrit. Res.* 22: 859-866 (2002); Milner, "A historical perspective on garlic and cancer," *J. Nutr.* 131: 1027S-1031S (2001) and Chen et al., "Apoptosis of hepatoma cells SMMC-7721 induced by *Ginkgo biloba* seed polysaccharide," *World J. Gastroenterol.* 8: 832-6 (2002); Winther et al., "Effects of *Ginkgo biloba* extract on cognitive function and blood pressure in elderly subjects," *Curr. Therap. Res.* 59: 881-888 (1998). The inventor observed that extract of orchid has an potent anti-inflammatory activity, possibly due to the decrease of *chlamydia* LPS (a potent activator of macrophages and lymphocytes; and extracts of other plants for example, but not way of limitation, *Gingko biloba*, Ginseng and Zingiber present an important vasodilation activity. These properties may be useful for treating skin lesions, hypertension and male erectile dysfunction.

The inventor has observed that extract of orchid has an potent anti-inflammatory activity, possibly due to the decrease of *chlamydia* LPS (a potent activator of macrophages and lymphocytes. Extracts of other plants, for example, but not way of limitation, *Gingko biloba*, Ginseng and Zingiber, possess potential important vasodilation activity. These properties may be useful for treating skin lesions, hypertension and male erectile dysfunction.

The extract from plants may be obtained by adding a solvent, such as alcohol to the plants, for example in the proportion 40:60 of vegetable:alcohol by weight, respectively. A range from 30:70 to 50:50 of vegetables:alcohol weight can be used. Ethanol, methanol, cereal alcohol may be used as the solvent.

In an embodiment of the invention, *Ginkgo biloba* leaves or chopped garlic cloves are placed in grain alcohol in a 40:60 w/w proportion for aging.

The aging process occurs by placing the vegetable mass/alcohol mixture in a dark and anaerobic ambient for 15 days or more. This step promotes the proliferation of the particles and enriches the population of particles.

The aging process may involve the use of extremely elevated or low pH and/or extremely elevated temperature and/or solvents.

In order to obtain the nanosized particles, a sequence of different systems of filtration may be used in order to concentrate the smallest, but heaviest particles. An enriched and aged extract can be filtered in a vacuum chamber, with 47 mm diameter glass microfibre filter, having a pore size of 1.1 µm. The solution can be filtered in Minitan Ultrafiltration System that is a tangential flow device with a microporous membrane GVLP OMP04, Durapore, that retains particles larger than 0.2 µm. The filtered solution was filtered again in the same system, using higher pressure of around 15 psig with the membrane PTTK OMT 04, polysulfone, having a retention rating of 30,000 NMWL. The process causes the retention of larger and heavier particles, expelling water and the lighter particles which are the empty and lighter archaea.

The first filtration retained the larger archaeas, bacteria, cell debris and viruses and was discarded. The filtered solution contained the smallest archaea and nanoarchaea. The second filtration retained the small archaea and nanoarchaea and expelled water and lighter particles that are of those with empty aspect, probably containing gases (that were considered pathogenic causing oxidation of the host cell and have to be excluded in case of use for treatment of subjects). The second retained solution is the preferred composition to be used. This system of filtration creates a highly concentrated solution of small particles comprised mainly of dense archaea and nanoarchaea and almost free of empty particles. The present method produces a composition having a concentration of small (less than 500 nm) and medium particles (between 500 nm and 1.1 µm) and was free of larger particles and/or empty particles.

The presence of other undesirable microorganisms, such as mycoplasmas, chlamydias and viruses, are be evaluated through electron microscopy, PCR, or quantitative real time PCR.

Alternatively, the particle may be derived from thermal water, where archeae reside. Such waters are rich in bicarbonate of sodium, carbonate of sodium and chlorite of sodium, having a high alkaline pH, and small amounts of metals such as lithium, strontium, ferric oxide, silica and alumina.

The same procedure of filtration may be performed to concentrate archaea and clean the thermal water from the other contaminants. However, variations on the Minitan Ultrafiltration System, tangential flow device, with larger pores, and the separation of different types of microorganisms may be required for best combinations between the size of the pore with the speed (that is done by the pressure). The presence of microorganisms in the retained or filtered solutions is evaluated by electron microscopy analysis.

The present invention also provides for methods of preventing and/or treating conditions characterized by undesirable cell proliferation, and infection by mycoplasma and/or non-mycoplasma microorganism. The method comprises administering to a subject a composition comprising one or more agent present in an effective amount to prevent growth or decrease the number of mycoplasma and/or non-mycoplasma microorganism in the subject.

Preferably, where mycoplasma co-infection already exists, the level of co-infection is decreased by at least ten percent. The level of co-infection may be measured by the number of mycoplasma or non-mycoplasma-associated microorganism present in a tissue or fluid sample, by the immune reaction toward it in the subject, or by any standard laboratory diagnostic assay against these microorganisms. The term "amounts effective" or "effective amounts" mean that the composition comprises agents that are capable of preventing or inhibiting growth of mycoplasma or non-mycoplasma-associated microorganism. The number of mycoplasma or non-mycoplasma-associated microorganism in the subject upon administration of the composition would decrease by at least ten percent of the original number of total microorganism in the subject prior to administration of the composition. Preferably, the number of microorganisms present in the subject would decrease by at least twenty percent, and more preferably, at least thirty percent.

The subject may be a human or non-human subject, and the term "mycoplasma-associated microorganism" or "non-mycoplasma microorganism" as used herein may refer to microorganism capable of infecting a human and/or a non-human host.

The amount of agent in the composition required to confer a therapeutic benefit may vary from patient to patient and depending on the nature of the condition should be treated. Thus, the doses may require adjustment as would be apparent to the skilled artisan.

Where the composition administered is derived from a plant extract, the subject receives one or two drops of the composition twice a day.

The period of treatment may be for one day or may extend for an indefinite period of time, including continuous use for years. Preferably, the treatment period is between 1 and 8 weeks.

The route of administration may be topical, intravenous, intraperitonial, intrathecal, oral, by inhalation, subcutaneous, intramuscular, or any other appropriate route.

Effective treatment may be evaluated by visual inspection of cellular tissue or of the serum. Fragmentation of the mycoplasmas into smaller fragments, intense aggregation and contraction of the archaea and mycoplasma or disppearance of them from the lesions are indications of the elimination of these microorganisms in the subject.

The success of the treatment may be evaluated by visual analysis of the archaea and/or mycoplasmal and/or chlamydia and/or spirochete forms or their products in the serum or in the lesions. The inventor has also discovered that the *lipoprotein* from Mycoplasma pneumoniae and LPS from *Chlamydia pneumoniae* may be detected in the serum, by immunoelectron microscopy, as presented in Example 14.

The present invention may be used to treat disorders associated with undesirable cell proliferation, including neoplasmas, malignancies, and atherosclerosis, and in preferred embodiments, the undesirable cell prolferation with fibrosis or sclerosis. Disorders characterized by undesirable cell proliferation associated with fibrosis include organ sclerosis, for example glomerulonephritis and glomeruloesclerosis associated with diabetes, aortic valve stenosis, cirrhosis, neoplasia, etc., and cutaneous thickening, including but not limited to chronic dermatitis, psoriasis, seborreic keratosis, baldness, etc.

Cell proliferation has been observed in the calcified fibrotic tissue in aortic valve stenosis process, where it was detected association of *Chlamydia pneumoniae* and Mycoplasma pneumoniae in large number; the excessive fibrosis in several parts of the body as in chronic hepatitis caused by viruses, Schistosomiasis, alcoholism; glomerulopathies, such as chronic glomerulonephritis, glomerulonephritis in systemic lupus erythematosus, focal segmental glomerulosclerosis, glomerulosclerosis in diabetic nephropathy, etc; arthritis and arthrosis in general; chronic encephalopathies, such as, Multiple Sclerosis, Alzheimer's Syndrome, chronic otitis, etc.

Analyzing some of these diseases, such as aortic valve stenosis of the elderly, neoplasias, baldness, chronic fibrosing hepatopathy and glomerulonephritis, the presence of large amount of archaea in the fibrosis has been observed, often in close contact or fused with mycoplasma and chlamydia. The presence of archaea inside the parenchymatous cells and macrophages, in the reticulum tubular system, which were dilated, was also observed.

The present invention shows that the cell proliferation associated with fibrosis found in several chronic diseases is coincident with the presence of archaea in close association with mycoplasma and/or chlamydia. Treatment of these microorganisms may decrease or prevent the cell proliferation and consequently the associated fibrosis.

To prevent frequent associated symptoms of malignant neoplasias and other chronic diseases, such as cachexia, leukopenia or anemia, effective doses of prolactin and growth hormone may be administered.

Other embodiments of the invention provide treatments for baldness and/or prostate cancer. Common mechanisms may underlie the pathogenesis of baldness and prostate adenocarcinoma as both processes are androgen dependent. Bald men have been found to exhibit a tendency to develop of prostate adenocarcinoma. See Timms, "Vertex baldness link to prostate cancer," *Lancet Oncology* 3:584 (2002); Giles et al., "Androgenetic alopecia and prostate cancer: findings from an Australian case-control study," *Cancer Epidemiol. Biomarkers Prev* 11: 549-553 (2002).

EXAMPLE 1

Mycoplasma, Chlamydia and Archaea Co-Infection in Aortic Valve Stenosis

It was shown, using electron microscopy, in situ hybridization and immunohistochemical techniques, that Mycoplasma pneumoniae in association with *Chlamydia pneumoniae* is related to the presence of aortic valve stenosis in certain elderly patients. Large numbers of *Chlamydia pneumoniae* (frequently degenerated) have visually calcified foci. Proliferation of *chlamydia* seems to be, at least in part, due to some kind of interaction with Mycoplasma pneumoniae that results in inflammation and fibrosis surrounding the focus of bacterial proliferation, and that culminates in calcium deposition.

Figure 2:
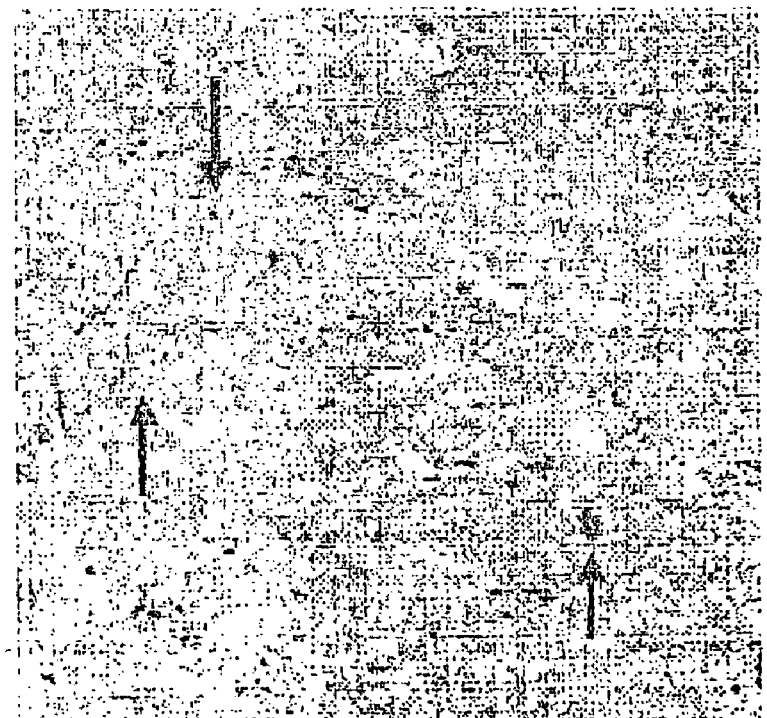
FIG. 2 is a histological section of human stenotic aortic valve with calcification, showing positivity for Mycoplasma pneumoniae's DNA (arrows) in the calcified foci (in situ hybridization technique—original magnification: 40×).

In particular, three regions of stenotic aortic valves (SAV) with calcification were studied: a) foci of calcification; b) peri-calcification fibrosis; and c) remaining valvular tissue. Histological sections from 14 aortic valves of patients undergoing valve replacement due to SAV were studied using immunohistochemistry to detect *Chlamydia pneumoniae* (CP) and in situ hybridization to detect Mycoplasma pneumoniae (MP) DNA. Other fragments were processed for electron microscopy. The mean fraction areas positive for CP antigens and MP DNA were obtained. This study showed that MP and CP are significantly increased in the calcified foci of SAV. The surrounding fibrotic tissue also had an increased amount of CP but not of MP. The Spearman correlation test demonstrated a significant correlation between quantity of MP in the more preserved regions of the valves and the amount of CP in the fibrotic regions. This finding suggested that other local factor is acting in such interaction (FIG. 1 and FIG. 2). These experiments were reported in Higuchi et al., "Mycoplasma pneumoniae and *Chlamydia pneumoniae* in calcified nodules of aortic stenotic valves," *Rev Inst Med trop S.Paulo* 44:209-212 (2002), published after the priority date of this application.

Figure 3:
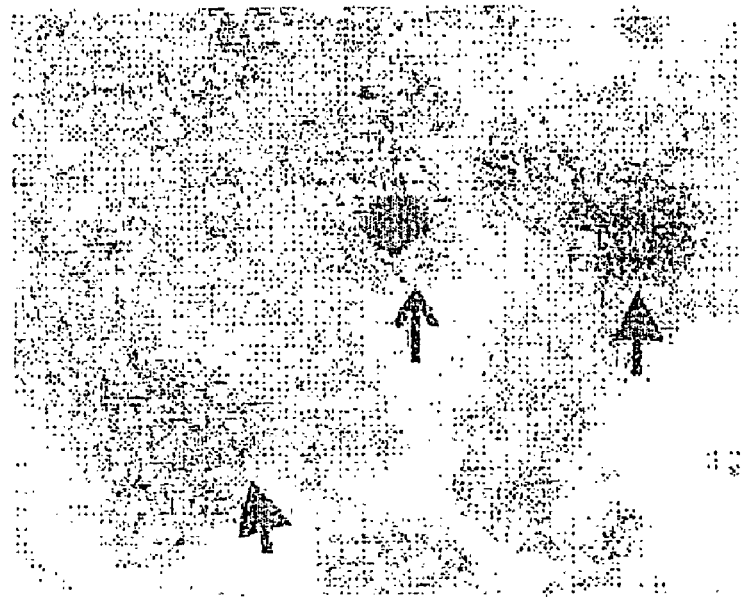
FIG. 3 is an electron micrograph of human stenotic aortic valve with calcification, showing the presence of mycoplasma associated to elementary body of *Chlamydia pneumoniae* (open arrow) and mycoplasma associated with archaea (closed arrows) nearby the calcification foci.
Figure 4:
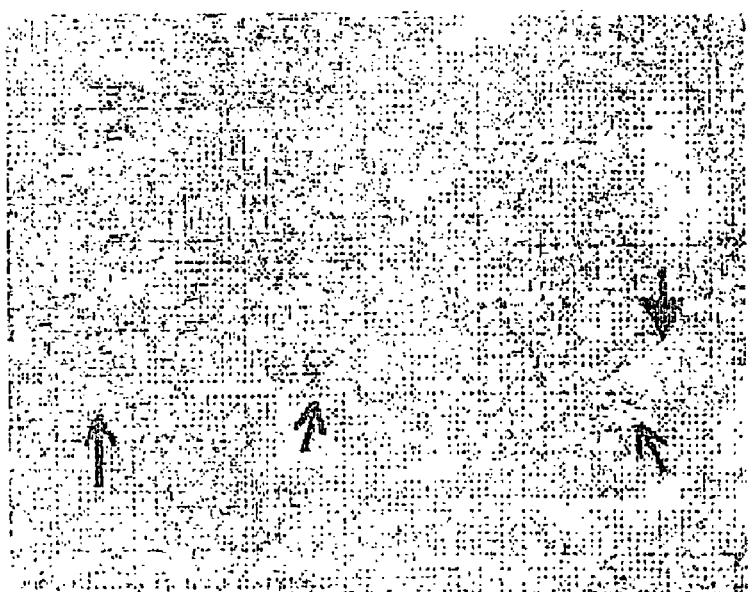
FIG. 4 shows a high quantity of mycoplasma (closed arrows) and elementary bodies of *Chlamydia pneumoniae* (open arrows) in calcified foci, most part with degenerated aspect.
Figure 26:
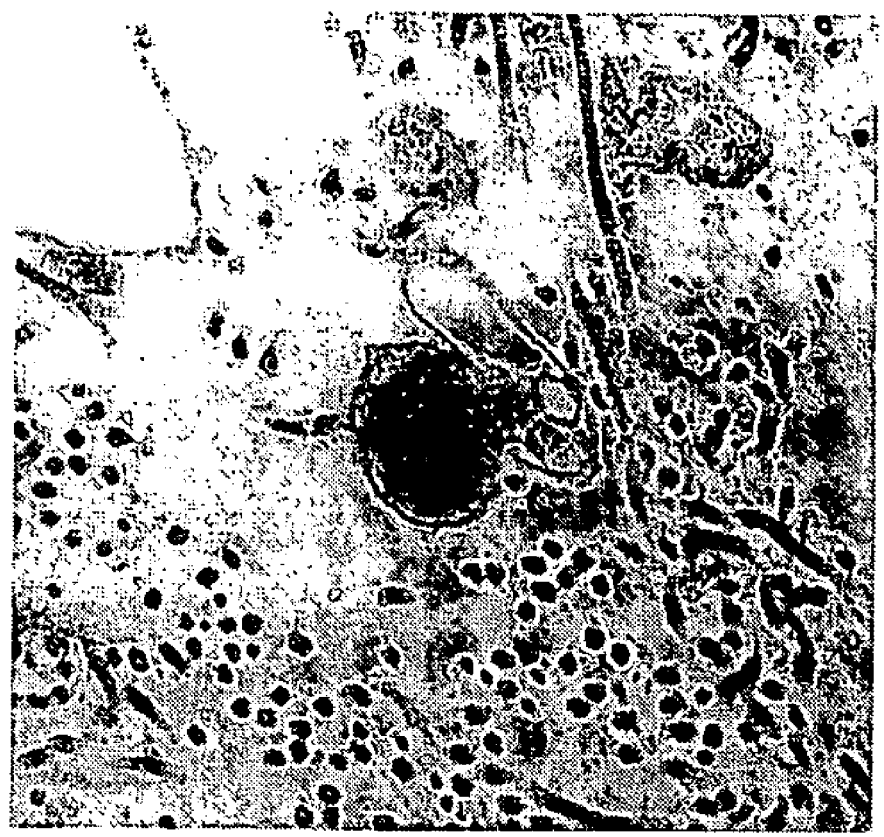
FIG. 26 shows an electron micrograph of a human stenotic aortic valve exhibiting microoganisms in intimate association, a *chlamydia* (rounded electron dense involved by double membrane structure) and a cylindrical structure which is involved by double thin monolayer lipidic membrane compatible with an archaea presenting empty aspect. Two rounded small structures involved by membrane, one is compatible with mycoplasma as contains granulous material inside and the other is compatible with an organelle of the archaea, are observed.

Electron micrographs also showed a large number of mycoplasma and chlamydia but also many rounded structures having two wavy membranes, suggestive of archaea. Many times these microorganisms seemed to be degenerated when in the calcified foci. In the pericalcified tissue, these microorganisms were more preserved, frequently assuming new forms through intimate contact or fusion of different microorganisms (FIG. 3 and FIG. 4). A close view of the intimate association of mycoplasma, chlamydia and archeae is also shown in FIG. 26.

EXAMPLE 2

Association of Mycoplasma, Chlamydia and Archaea Co-Infection with Chronic Glomerulonefritis It was shown that laboratory rats usually present severe pulmonary injury by natural chronic infection due to Mycoplasma pulmonis and Chlamydia pneumoniae See, Damy et al,. "Coinfection of laboratory rats with Mycoplasma pulmonis and *Chlamydia pneumoniae*," *Contemp.Top.Am. Assoc.Lab.An.Sci.* 42: 52-56 (2003).

Figure 5:
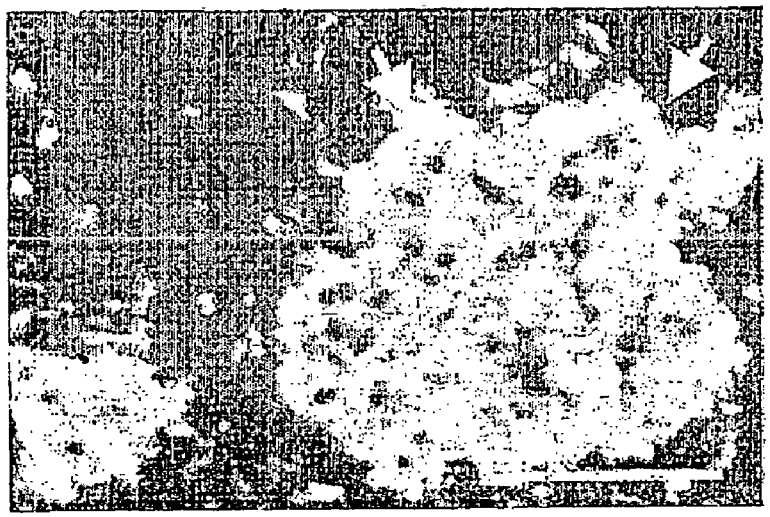
FIG. 5 shows a histological section of a kidney from rat having a pulmonary infection infected by Mycoplasma pulmonis and *Chlamydia pneumoniae* and presenting chronic glomerulonephritis, showing intense deposits of Mycoplasma pulmonis antigens in the basal glomerular membrane. (Confocal microscopy exhibits double staining immunofluorescence technique: fluorescein—detection of Mycoplasma pulmonis antigens on the glomerular external surface—arrows, rhodamine in dark staining detection of vimentin in the center of glomerulus representing the mesangial cells and a double staining representing simultaneous positivity for vimentin and Mycoplasma pulmonis antigens that corresponds to a clear layer at the glomerulus periphery that is probably the capillaries zone).

These animals also presented proliferative and/or focal sclerosis glomerulonephritis associated with interstitial chronic inflammation, with calcification and atrophy of the parenchyma, as presented by immunohistochemistry and immunofluorescence of chlamydia and mycoplasma antigens in renal tubules and glomeruli (FIG. 5). Using of electron microscopy, the presence of archaea in an isolated form, or in close association with the mycoplasma and/or *chlamydia* was also observed.

EXAMPLE 3

Figure 6:
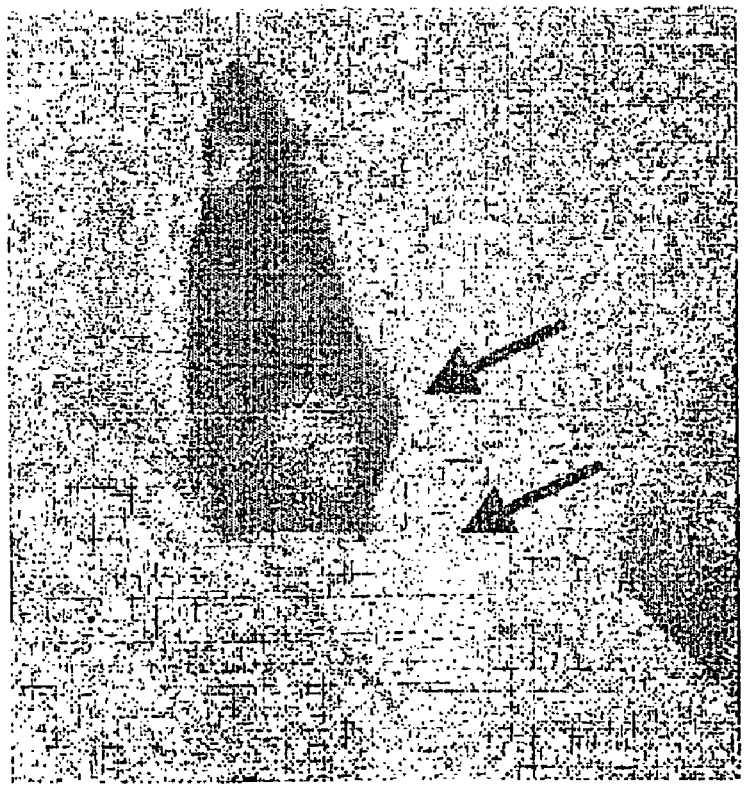
FIG. 6 shows a photo of a rat with ulcers in its back and tail (arrows) due to infection caused by mycoplasma, chlamydia and spirochetes.
Figure 7:
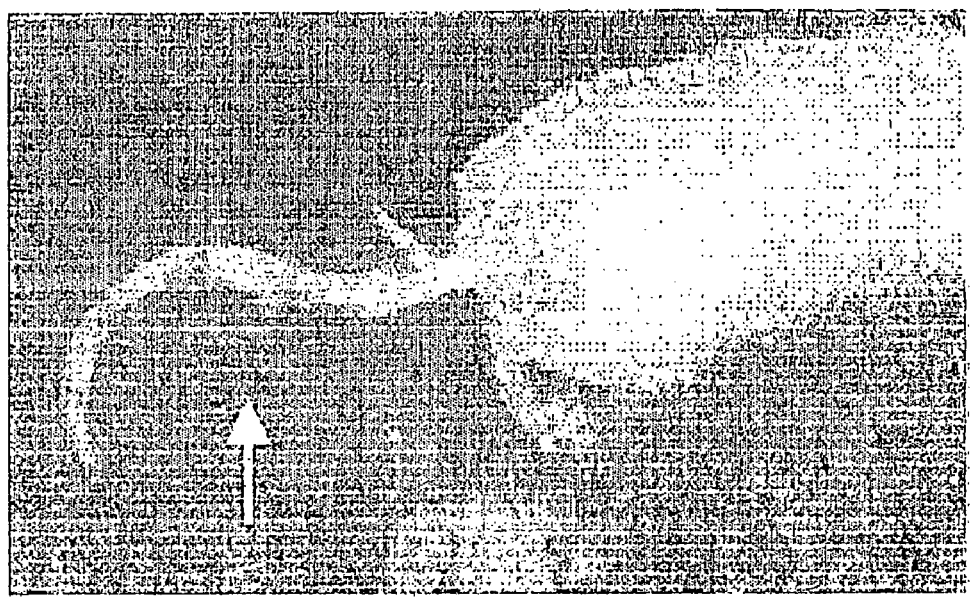
FIG. 7 shows an ulcer in a rat tail (arrow) infected by mycoplasma, chlamydia and spirochete.
Figure 8:
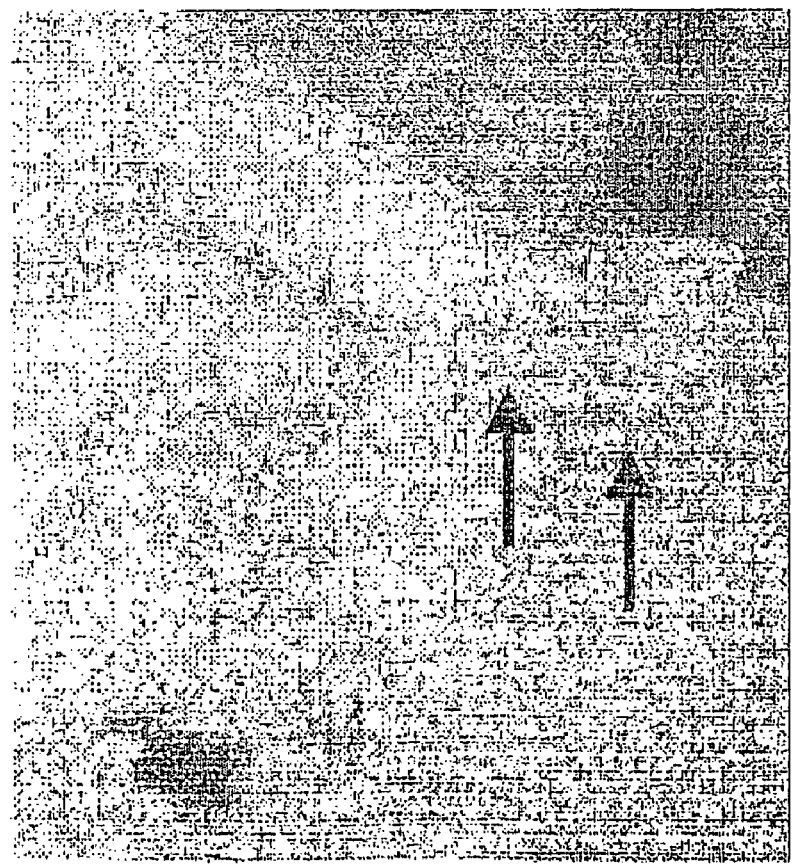
FIG. 8 shows a rat with ulcers and lesions in the articulations and in the legs (arrows) or ulcers in the thorax, which are infected by mycoplasma, chlamydia and spirochete.
Figure 9:
FIG. 9 shows an electron micrograph of a rat lesion characterized by a skin ulcer presenting mycoplasmas (thick arrows), some of them containing *chlamydia* (thin arrow) and spirochete (arrow-head).
Figure 10:
FIG. 10 shows an electron micrograph of a lesion from a rat skin ulcer presenting a high quantity of mycoplasma (thick arrow) in close association with other microorganisms such as *chlamydia* (thin opened arrow).
Figure 11:
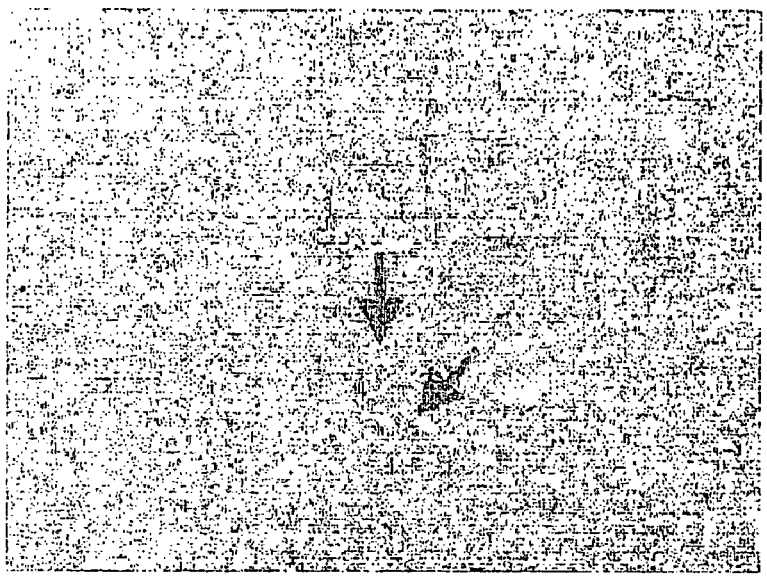
FIG. 11 shows a histological section of the lesion of the rat's tail exhibiting structures similar to spirochete (arrows) in necrotic skin tissue (Warthin-Starry's coloration—original magnification: 63×).

Association of Mycoplasma and Spirochetes Co-Infection with Ulcerative Skin Lesions and Articular Diseases in Rats and Mice Laboratory animals (rats and mice) from the Animal House of the São Paulo University School of Medicine exhibited spontaneous disease characterized by skin ulcers, loss of tail, ulcer of paw with injury of the joins (FIG. 6, FIG. 7 and FIG. 8). The histology showed chronic inflammatory process with large numbers of plasma cells, lymphocytes and foam macrophages in the ulcers, associated with vasculitis and microvascular thrombosis. Electron microscopy showed the association of mycoplasma and *chlamydia* and/or structures compatible with spirochete and/or their fragments (FIG. 9 and FIG. 10). The specific staining technique Warthin Starry demonstrated many positive silver stained structures suggestive of spirochetes (FIG. 11).

EXAMPLE 4

Treatment of Co-Infected Rats with Mycoplasma and Spirochete with Trans-Sialidase of *Trypanosoma cruzi*

Figure 12:
FIG. 12 shows the rat from FIG. 6 having clearly delimited skin ulcers in the back and in the tail (arrows) indicating beginning of healing after 4 days of treatment with trans-sialidase of *Trypanosoma cruzi*, native form.
Figure 13:
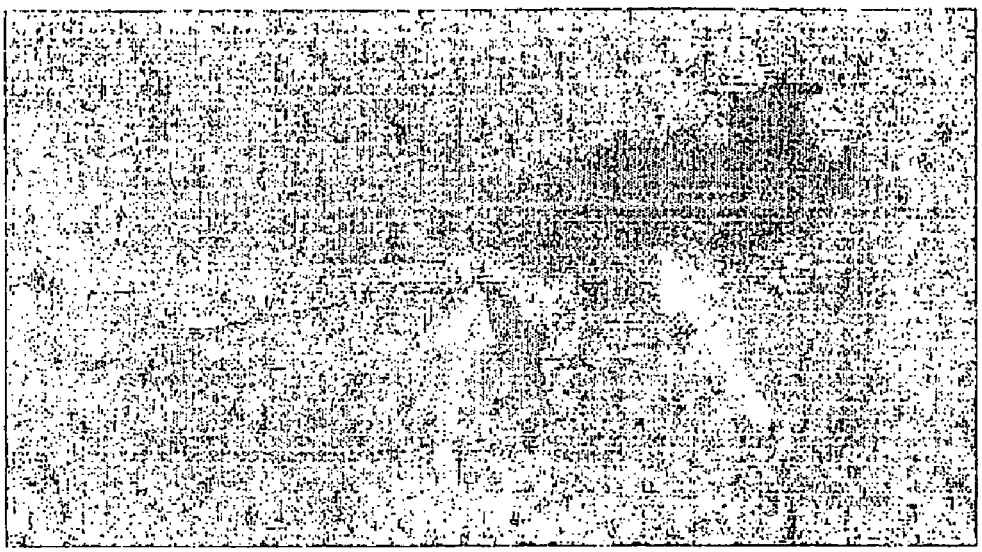
FIG. 13 shows the rat of FIG. 6 having lesions that are healed, showing skin over in the tail and back (arrows) after 14 days of treatment with trans-sialidase of *Trypanosoma cruzi*, native form.

Two rats presenting skin ulcer and tail injury were treated. One received 0.5 ml/animal of TSN (complete active native trans-sialidase of *T. cruzi*), every day for 10 days, and other TSC (active trans-sialidade substance catalytic portion) for 8 days. TSC was produced from a recombinant bacteria containing the plasmidium pTSII (deposited in the American Type Culture Collection (ATCC) bank of genes, with the number PTA-3483). They were killed respectively in 14 and 10 days. The skin ulcers showed initial healing after 4 days of treatment, with better defined limits (FIG. 12) and complete healing in 14 days, and the formation of a new coat (FIG. 13). The tail did not fall off and histological examinations demonstrated regression of the lesion and severe decrease of all infectious agents.

EXAMPLE 5

Figure 14:
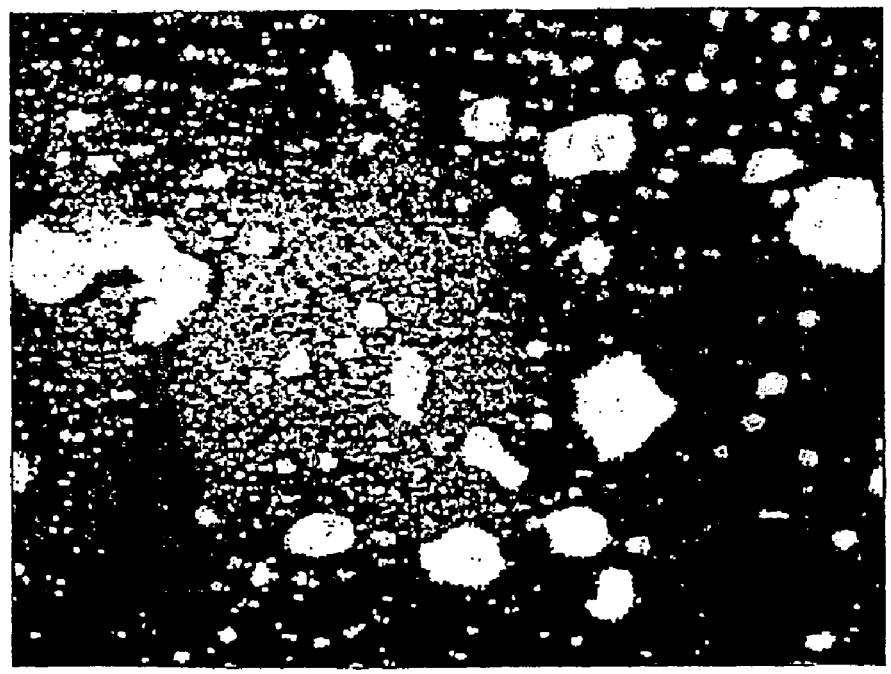
FIG. 14 shows a confocal micrograph of a solution containing archaea and nanoarchaea derived from the plant *Ginkgo biloba* stained with acridine orange vital stain. The larger rounded particles are compatible with archaea, the smaller rounded or cylindric particles are compatible with nanoarchaea and the brilliant points adhered to the surface of archaea and to the extremity of nanoarchaea which were detected by the reflected light channel may correspond to metal (The reflected channel detect metal).
Figure 15:
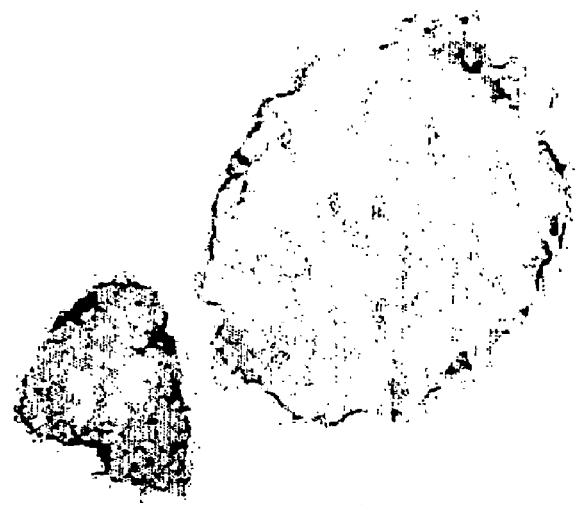
FIG. 15 shows the presence of archaea with the characteristic double-wrinkled-envlotory monolayer lipid membrane that presents many points of interruption in a solution obtained from crushed leaves of *Ginkgo biloba*. Also observed is a smaller archaea that is less electron dense and may correspond to a nanoarchaea. Compared with the archaea from garlic extract described below, the archaea from *Ginkgo biloba* extract is smaller.
Figure 16:
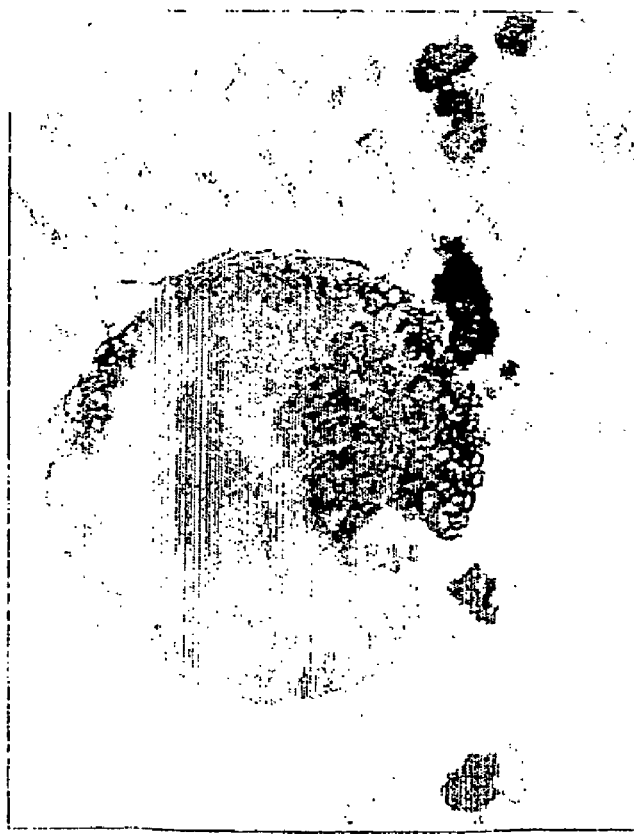
FIG. 16 shows an electron micrograph of an archaea present in an extract of garlic cloves exhibiting double-wrinkled monolayer lipid membrane and presenting many surrounded small structures (nanoarchaeas) that may be linked to some metal as they have dark electron dense points.

Demonstration of Archaea Cultured from *Ginkgo biloba* and *Allium sativum* Extracts The alcoholic and anaerobic atmosphere present in plant extract is favorable to proliferation of archaea. Green leaves of *Ginkgo biloba* and cloves of garlic were ground and put to age in cereal alcohol PA according to the procedures described in the Detailed Description of the Invention. These produced solutions rich in archaea. Archaea present in extracts from *Ginkgo biloba* and garlic were examined using fluorescence microscopy and presented the characteristics: a roundness shape and surrounded by many other smaller structures which seemed to contain metals because when analyzed at the confocal laser microscope they are seen by the reflected channel which is for detection of metals. The larger and smaller rounded structures are stained by the acridine orange vital stain that impregnates DNA and represent the archaea and nanoarchea. The brilliant points in contact with these structures are likely to be metal as they were detected in the reflected light channel. Archaea present in *Ginkgo biloba* extract are smaller and carry much more bright points (metals) (FIG. 14) than those present in extracts from garlic. Electron microscopy demonstrated that the above described structures were typical of archaea, i.e. having a double, wrinkled and interrupted envoltory membrane. The smaller structures surrounding the archaea are likely to be nanoarchaea. Archaea cultivated from the extract of *Ginkgo biloba* (FIG. 15) are smaller than those present in extract of garlic (FIG. 16).

EXAMPLE 6

Treatment of Facial Epidermoid Carcinoma from a Cow

Figure 17:
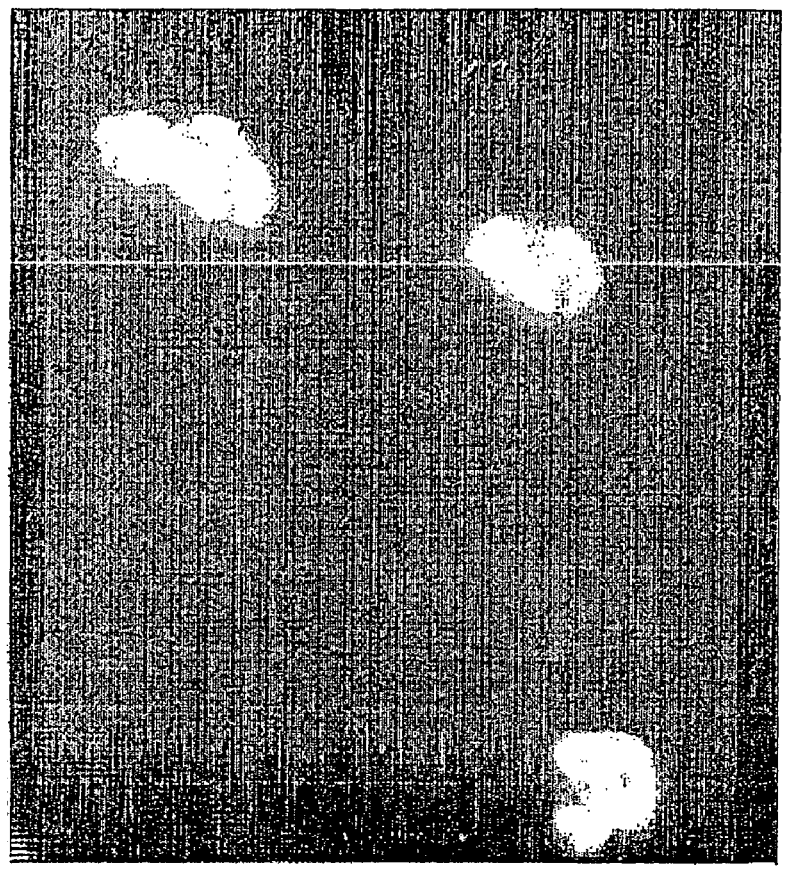
FIG. 17 shows a fluorescent micrograph of serum from a cow exhibiting epidermoid carcinoma, where the animal was treated with trans-sialidase enzyme and the serum exhibited several small large rounded structures, usually in pairs, that stained with a vital stain acridine-orange that may be compatible with pathogenic archaeas.

A cow exhibiting a wide epidermoid carcinoma covering the left side of the face including the eye, was treated. Two ml of native trans-sialidase (supernatant of *T. cruzi* culture, as described in the first priority) was injected in the tumor, on alternate days. The tumor showed a fast regression, decrease in the main dimensions at the palpation, and the ulcer also decreased from 8 to 2 cm after 12 days of treatment. The cow also exhibited a fast weight loss, weakness and was killed after the end of this period of treatment. The serum analysis at the fluorescence microscope revealed by the use of vital staining (acridine orange), many forms compatible with mycoplasma, large archaea (FIG. 17) and *chlamydia* in movement. The electron microscopy confirmed this finding.

EXAMPLE 7

Treatment of Experimental Adenocarcinoma in Rats (Walker Tumor) that are Co-Infected with Mycoplasma and Pathogenic Archaea, using Trans-Sialidase of *Trypanosoma cruzi*, Extracts from Plants, PDTC, Growth Hormone and Prolactin Malignant neoplasia was induced experimentally by inoculation of 500,000 cells of adenocarcinoma of Walker in the right flank of several rats in order to verify if the use of simultaneous anti-proliferative and anti-oxidative drugs may decrease the growing of the neoplasia and the level of metastases. Usually the animals receiving such inoculation of adecarcinoma cells survived for 10-12 days and presented metastasis to many ganglia, liver and lung. Nine of these animals were inoculated after 7 days of tumor cells with 0.5 ml of trans-sialidase TS (supernatant of culture of *T. cruzi*) as described in the U.S. patent application Ser. No. 10/086,913, filed Mar. 1, 2002 and with 0.75 mg of PDTC, into the peritoneum every day. The particles containing DNA or RNA prepared from plant extracts (garlic, *Ginkgo biloba* and tomato) as described above was also administered. All animals received 0.5 ml of garlic extract by subcutaneous route (Table 1 below). The tumors were similar in size for all animals at the beginning of the treatment, i.e. 2.8×2.7 cm.

Rats 1-4 were followed until death. Rats 3 and 4 received 0.5 ml of *Ginkgo biloba*'s extract, every day. The tumors increased slower in all 4 animals receiving plant extracts than the controls. However, the group treated with garlic and *Ginkgo biloba* extract had a higher survival time.

Rats 1 and 4 died after 12 days of treatment and rat 2 and 3 died after 19 days. The necropsy demonstrated that the tumor in Rat 4 had a smaller size of the tumor with less microscopic necrosis than Rat 1, suggesting that the addition of prolactine helped the anti-cancer therapy.

From the 12th day of treatment, Rat 2, that received trans-sialidase and garlic extract, also received prolactine and growth hormone. Rat 3 treated with *Ginkgo biloba*, received only growth hormone. Both animals died after 19 days of treatment. The animal that received both prolactin and growth hormone showed lower tumor dissemination than the animal that received only the growth hormone, suggesting that the prolactine prevented the growth hormone bad effects.

In Rats 1-4, a decrease in the number of the white cells and red cells in the blood was observed as is usual in animals with cancer.

Prolactin and/or growth hormone administration to diminish these effects was also evaluated. Intraperitoneal injection of prolactin (0.5 ml per animal) and/or growth hormone (0.5 ml per animal) for 7 days was performed. Rats 5 and 7 also received 0.5 ml of tomato and 0.5 ml of garlic extracts, injected directly into the tumor. Rats 6, 8 and 9 received tomato extract through a subcutaneous route. Rats 5 and 6 received a dose of 0.026 mg of growth hormone, and the rats 7 and 8, a dose of 0.1 mg of ovine prolactine from Sigma intraperitonially. Rat 9 received simultaneously 0.1 mg of prolactine and 0.026 mg of growth hormone. Rats 5-9 showed a decrease in the tumor growth, and a better clinical general aspect, characterized by the amount of weight loss, decrease mobility and lack of hair, compared with the non-treated animals. The association of the three extracts derived from three medicinal plants (garlic, *Ginkgo biloba* and tomato), the enzyme TS, prolactine and growth hormone was the treatment that had the best result in reducing the size and dissemination of the neoplasia (Rat 9). Usually, this type of neoplasia causes death of the animal in less than 12 days. The only animal that showed regression of the tumor after 7 days of treatment was the rat 8 that had received the 3 plant extracts and prolactine, in association with TS. This experiment indicated the need of a wide association of different agents used in combination to combat neoplasia.

mycoplasma in the hepatocytes, Kupffer cells, Disse space and in the vascular lumen, mainly in the animals that developed granulomas.

Treatment with 0.1 ml of trans-sialidase (TSN) and 0.2 ul of extract of *Ginkgo biloba* intraperitoneal prepared as described above, decreased significantly the numbers of archaea present in the hepatocytes and in the Disse space, as shown in Table 2 below. Archaea was observed to be compatible with that provenient from *Ginkgo biloba*'s extract which is more electron dense. It adhered to a mycoplasma and two probably pathogenic empty archaea, in the extracellular space (FIG. 18).

TABLE 2

Count of mean numbers of archaea in 35 mm photos (720× magnification) of the hepatocyte or in the Disse's space in electron micrographs

| Group of mice | Non treated hepatocyte | Treated hepatocyte | Non-treated Disse's space | Treated Disse's space |
|---|---|---|---|---|
| Mean | 25.7 | 12.7 | 10.8 | 6.2 |
| SD | 32.7 | 12.5 | 6.3 | 3.8 |

SD—standard deviation

EXAMPLE 9

Anti-Mycoplasma Treatment with Medicinal Thermal Water

The thermal waters from Brazil, considered one of the best medicinal waters, contains large numbers of archaea. These waters are rich in bicarbonate of sodium, carbonate of sodium and chlorite of sodium, having a high alkaline pH, and small amounts of metals such as lithium, strontium,

TABLE 1

Schedule of treatment for each Rat for Example 7

| | Rat No. | | | | | | | | |
|---|---|---|---|---|---|---|---|---|---|
| | 1 | 2 | 3 | 4 | 5 | 6 | 7 | 8 | 9 |
| TS + PDTC | + | + | + | + | + | + | + | + | + |
| Garlic | + | + | + | + | +* | + | +* | + | + |
| Ginkgo | − | − | + | + | + | + | + | + | + |
| Tomato | − | − | − | − | +* | + | +* | + | + |
| Prolactine | − | + | − | + | − | − | + | + | + |
| Growth Hormone | − | + | + | − | + | + | − | − | + |
| Treatment days | 12 d⊕ | 19⊕ | 19⊕ | 12⊕ | 7 | 7 | 7 | 7 | 7 |
| Tumor size (cm) | 6.5 × 2.5 | 6.5 × 2.5 | 6.2 × 2.1 | 5.2 × 2.9 | 3.8 × 3.4 | 4.5 × 3.3 | 4.8 × 2.8 | 1.9 × 2.2 | 3.9 × 3.2 |

*injection in the tumor
⊕days of treatment until death

EXAMPLE 8

Treatment of Fibrosis Due to Experimental Chronic Hepatopathy Induced by *S. mansoni* Eggs in Mice Mice from isogenic BALBc and strain B4 were infected with 5 c of *S. mansoni* cercaria, that is the infectant form of the worm by subcutaneum, developed granulomas. In contrast, mice from the strain C57BL6, infected with the same number of cercarias did not develop such fibrosis. The electron microscopy showed large numbers of archaea and ferric oxide, silica and alumina. The metals are excellent sources of energy for archaea. A series of in vitro experiments with sera from human or animal presenting some of the chronic diseases above described were performed. A serum drop together with a drop of the thermal water were put on a slide, together with a drop of acridine orange (vital stain for intracellular DNA). The serum exhibited many irregular structures, in large amount, with morphology compatible with mycoplasma and frequently having archaeas adhered. The addition of garlic extract led to fragmentation of the mycoplasmas in smaller fragments. The addition of thermal water to extract from *Ginkgo Biloba* led to intense aggregation and contraction of the archaea and mycoplasma. Conditions that favor aggregation of mycoplasma and archaea may prevent their movement and may favor their elimination from the host.

EXAMPLE 10

Similarities of Infectious Agents Present in Baldness and in Adenocarcinoma of Prostate Favoring the infectious etiology in both processes, mycoplasma and archaea in skin samples from a subject's head in a baldness region and in biopsy from adenocarcinoma of prostate were observed. The morphology of archaea was similar in both conditions, were detected into the cells and also in the extracellular space by electron microscopy analysis. (FIG. 19 and FIG. 20).

EXAMPLE 11

Treatment of Baldness

In a subject presenting baldness, topical administration of 1:10 solution of supernatant of trans-sialidase in anionic gel, intercalated with topic administration of alcoholic extracts from *Ginkgo Biloba* and garlic 1:1 diminished the hair loss and the still existent hair became stronger. The composition was used daily for 3 months. The subject also reported an improvement of his sexual performance.

The patient also presented severe dandruff and an alcoholic extract of orchid was administered for five days. The treatment appeared to eliminate the dandruff after 3 days of application.

EXAMPLE 12

Interaction Between Archaea and Homeopatic Drugs and Metal Ion

Archaea present in extracts from plants have different characteristics each other. Those present in the tomato and guava extracts seem to be hyperthermophilics as they resist boiling. Adding a drop of culture of archaea or active nanoparticles containing DNA from extract of tomato plus a drop of homeopathic drug, such as carbonic calcarea and a drop of acridine orange vital stain, it was observed that the archaea move faster than without the homeopathic drug, to one side of the slide. The same procedure performed with a drop of extract from guava caused the DNA active nanoparticles to decrease in their movements, driving to an opposite side to the tomato's particles direction. Despite the similar morphology with archaea from *Ginkgo biloba*, archaea from garlic extracts cause a difference in the polarity of movement. Using the same test above described, adding a drop of garlic archaea, a drop of water solution of potassium sulphate and a drop of acridine orange it was observed that the archaea moved to one side of the slide and the archaea from *Ginkgo biloba* in the presence of zinc sulphate, moved to the opposite side. Archaea from *Ginkgo biloba* presented a stronger brightness than those of the garlic, observed at the fluorescence microscope.

EXAMPLE 13

Figure 21:
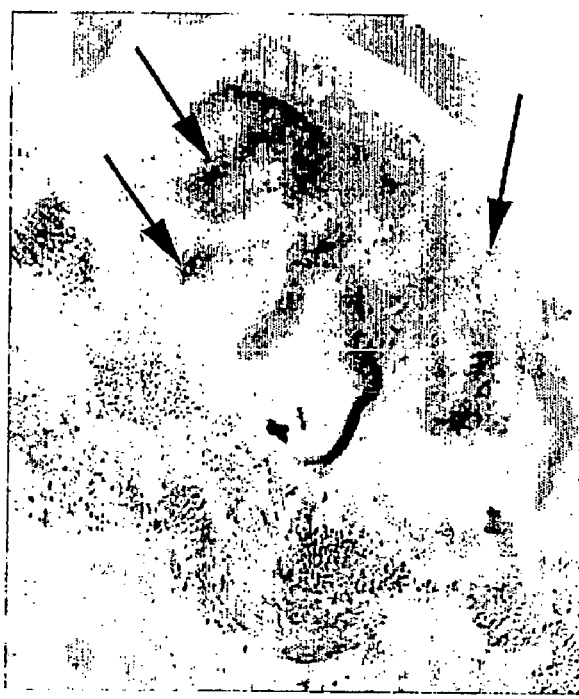
FIG. 21 shows an immunoelectron micrograph exhibiting antigens of Mycoplasma pneumoniae (arrows pointing to black dots) in a spirochete present in the skin lesion in rat with Lyme-like disease.
Figure 22:
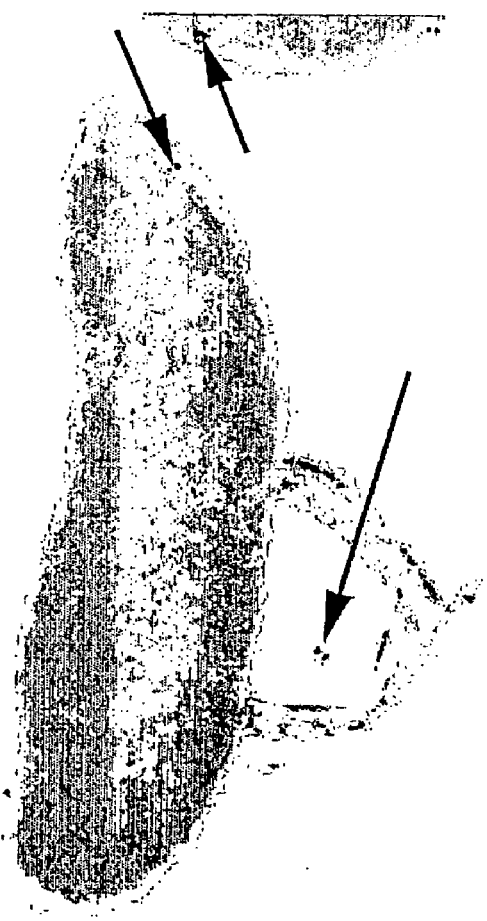
FIG. 22 shows an archaea adhered to a fragmented cell presenting antigens of Mycoplasma pneumoniae inside itself and also in the cytoplasm of the cells (arrows)
Figure 23:
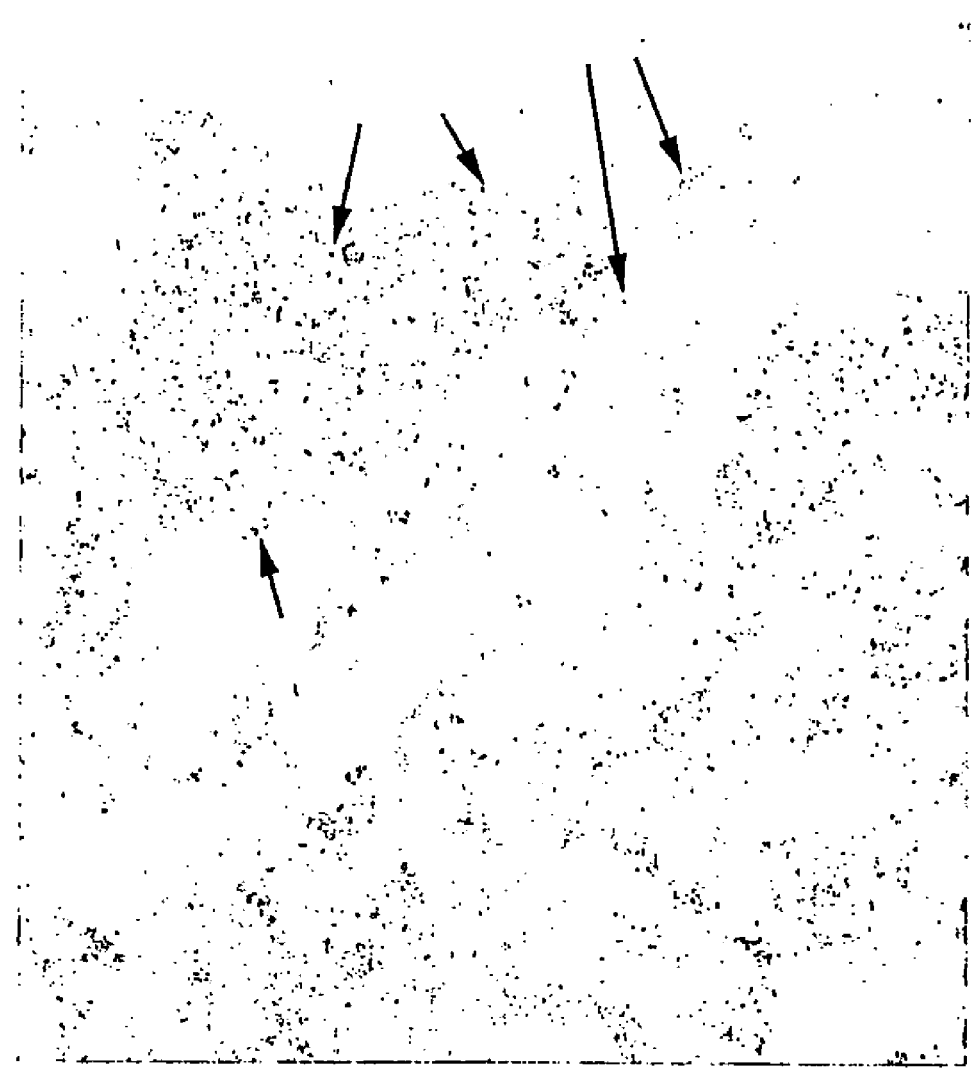
FIG. 23 shows several black dots that are marks of Mycoplasma pneumoniae antigens in adhesions between pseudopodes of a glomerulum from a rat with Lyme-like disease.

Demonstration by Immunoelectron Microscopy the Fusion of Mycoplasma Antigens with Archaea and Spirochete Using the immunoelectron microscopy and a specific monoclonal antibody against Mycoplasma pneumoniae clone M 2110181 from Fitzgerald Industries Intenational, Inc (Concord, Mass., USA) antigens of Mycoplasma pneumoniae, in rat presenting the Lyme-like disease as described above, are located in the spirochetes in the lesions (FIG. 21), in archaea that frequently are adhered to damaged red cells and in the cytoplasm of these red cells in the blood (FIG. 22). These antigens were also in the structures that cause adhesions of the pseudopodes of glomeruli from kidney presenting glomerulonephritis.

EXAMPLE 14

Evaluation of Serum Sample from Patient with Coronary Arteial Disease (CAD)

Lipoprotein from Mycoplasma pneumoniae and LPS from *Chlamydia pneumoniae* was detected in the serum, by immunoelectron microscopy.

One ml of serum from the patient was processed to detect lipid particles, such as archaea. Lipoprotein from Mycoplasma pneumoniae was in greater amount in the serum of atherosclerotic patients and LPS from *Chlamydia pneumoniae* was increased in the serum of patients with acute myocardial infarction. Particles of C reactive protein (CRP) were also detectable by immunoelectron microscopy and their number increased in correlation with the number of mycoplasmal lipoprotein. The mean numbers of CRP and Mycoplasma pneumoniae particles/$mm^2$ of electron microscopy photos were higher in CAD patients ($1.45 \pm 0.50$ and $1.32 \pm 1.35$) than in healthy subjects with similar age ($1.05 \pm 0.29$ and $0.26 \pm 0.20$) ($p<0.01$), and were correlated each other only in atherosclerotic patients group. Then, the success of the treatment may be performed counting the particles of *lipoprotein* from mycoplasma, LPS from *Chlamydia pneumoniae* or pathogenic archaea in the serum, as shown in FIG. 25.

The invention claimed is:

1. A method of treating a disorder characterized by undesirable cell proliferation associated with fibrosis in a subject comprising treating an underlying infection by mycoplasma and a second microorganism by administering an agent to the subject in an amount effective to decrease the number of mycoplasma and the second microorganism in the subject, wherein the agent comprises a particle selected from the group consisting of non-pathogenic archaea and non-pathogenic nanoarchaea.

2. The method of claim 1, wherein the second microorganism is selected from the group consisting of *chlamydia*, spirochaete, and pathogenic archaea.

3. The method of claim 1, wherein the disorder is selected from the group consisting of aortic valve stenosis with calcification, fibrotic glomerulopathy, Lyme's disease, fibrosing chronic hepatopathy, malignant neoplasia, cutaneous thickening, organ sclerosis, erectile dysfunction and arterial hypertension.

4. The method of claim 1, wherein the particle is prepared from plant extracts selected from the group consisting of Ginko biloba, garlic, orchid, tomato, and guava.

5. The method of claim 1, wherein the particle is prepared from a thermal water.

* * * * *

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: generic primer for archaea
```

```
<400> SEQUENCE: 1
agtcaggtaa cgagcgag                                                  18

<210> SEQ ID NO 2
<211> LENGTH: 17
<212> TYPE: DNA
<213> ORGANISM: Artificial Sequence
<220> FEATURE:
<223> OTHER INFORMATION: generic primer for archaea

<400> SEQUENCE: 2
gtgcaaggag cagggac                                                   17
```